(12) United States Patent
Siegel et al.

(10) Patent No.: US 9,658,224 B2
(45) Date of Patent: May 23, 2017

(54) PHAGE PARTICLE DIAGNOSTIC REAGENTS

(75) Inventors: Donald Siegel, Philadelphia, PA (US); Carlos F. Barbas, III, Solana Beach, CA (US)

(73) Assignees: The Trustees of the University of Pennsylvania, Philadelphia, PA (US); The Scripps Research Insitute, La Jolla, CA (US)

( * ) Notice: Subject to any disclaimer, the term of this patent is extended or adjusted under 35 U.S.C. 154(b) by 1696 days.

(21) Appl. No.: 12/085,618

(22) PCT Filed: Nov. 14, 2006

(86) PCT No.: PCT/US2006/044134
§ 371 (c)(1),
(2), (4) Date: Jul. 29, 2009

(87) PCT Pub. No.: WO2007/064462
PCT Pub. Date: Jun. 7, 2007

(65) Prior Publication Data
US 2010/0015595 A1 Jan. 21, 2010

Related U.S. Application Data

(60) Provisional application No. 60/740,440, filed on Nov. 29, 2005.

(51) Int. Cl.
*C12N 7/02* (2006.01)
*C12Q 1/00* (2006.01)
(Continued)

(52) U.S. Cl.
CPC ....... *G01N 33/555* (2013.01); *G01N 33/6854* (2013.01)
(Continued)

(58) Field of Classification Search
None
See application file for complete search history.

(56) References Cited

U.S. PATENT DOCUMENTS 3,717,705 A * 2/1973 Haimovich et al. .......... 436/519
5,876,925 A 3/1999 Siegel
(Continued)

FOREIGN PATENT DOCUMENTS

WO WO2004/027028 1/2004

OTHER PUBLICATIONS

Schaade et al., Journal of Clinical Microbiology, 2001, 39(10):3809.*
(Continued)

*Primary Examiner* — Janet L Andres
*Assistant Examiner* — M. Franco Salvoza
(74) *Attorney, Agent, or Firm* — Saul Ewing LLP; Kathryn Doyle

(57) ABSTRACT

The present invention relates to novel methods for detecting a member of a known binding pair in a sample, including a cell, where one member of the pair (termed the "receptor") is expressed by a bacteriophage, which phage is then used to detect the presence of the other member of the pair (termed the "ligand" or "target"). Rather than detecting the binding of the phage using antibody-based technology, the present invention relates to detecting marker molecule associated with the phage. In one aspect, the invention relates to identifying an antigen-bearing moiety (e.g., a red blood cell antigen) of interest present on a cell, e.g., a red blood cell, using antibody-displaying bacteriophage, as well as detecting anti-red blood cell auto- or alloantibodies and/or complement in a sample, using antiglobulin reagent-displaying bacteriophage and detecting a marker molecule associ-
(Continued)

ated with the phage. In one aspect, the phenotype of the phage is not linked with the genotype of the phage.

23 Claims, 12 Drawing Sheets

(51) Int. Cl.
*G01N 33/53* (2006.01)
*A61K 39/00* (2006.01)
*A61K 39/395* (2006.01)
*G01N 33/555* (2006.01)
*G01N 33/68* (2006.01)

(56) References Cited

U.S. PATENT DOCUMENTS

| | | | |
|---|---|---|---|
| 5,985,543 | A | 11/1999 | Siegel |
| 6,255,455 | B1 | 7/2001 | Siegel |
| 2002/0025536 | A1* | 2/2002 | Gyuris et al. ............ 435/7.1 |
| 2002/0110806 | A1* | 8/2002 | Merril ........................ 435/5 |
| 2005/0014261 | A1* | 1/2005 | Houtzager et al. ......... 435/456 |
| 2005/0136399 | A1 | 6/2005 | Siegel |
| 2005/0191622 | A1 | 9/2005 | Siegel |
| 2008/0305119 | A1* | 12/2008 | Dewhurst et al. ......... 424/178.1 |

OTHER PUBLICATIONS

Azbel, PNAS, 1979, 76(1):101-105.*
Baek et al., "An improved helper phage system for efficient isolation of specific antibody molecules in phage display," Nucleic Acids Research, vol. 30, No. 5 (e18)(2002).*
Barbas, 1995, Nature Medicine 1:837-839.
Chang and Siegel, 1998, Blood 91:3066-3078.
Chang and Siegel, 2001, Transfusion. 41:6-12.
Czerwinski et al., 1995, Transfusion. 35:137-144.
Czerwinski et al., 1999, Transfusion. 39:364-371.
de Kruif et al., 1995, J. Mol Biol. 248:97-105.
Siegel and Silberstein, 1994, Blood 83:2334-2344.
Siegel et al., 1997, J. Immunol. Methods 206:73-85.
Siegel, 2001, Transfus. Med. Rev. 15:35-52.
Green and Hughes, 2005, "The antiglobulin test." in Denise Harmening (ed.) Modern Blood Banking and Transfusion Practices, F A. Davis Company, Philadelphia, pp. 93-107.

* cited by examiner

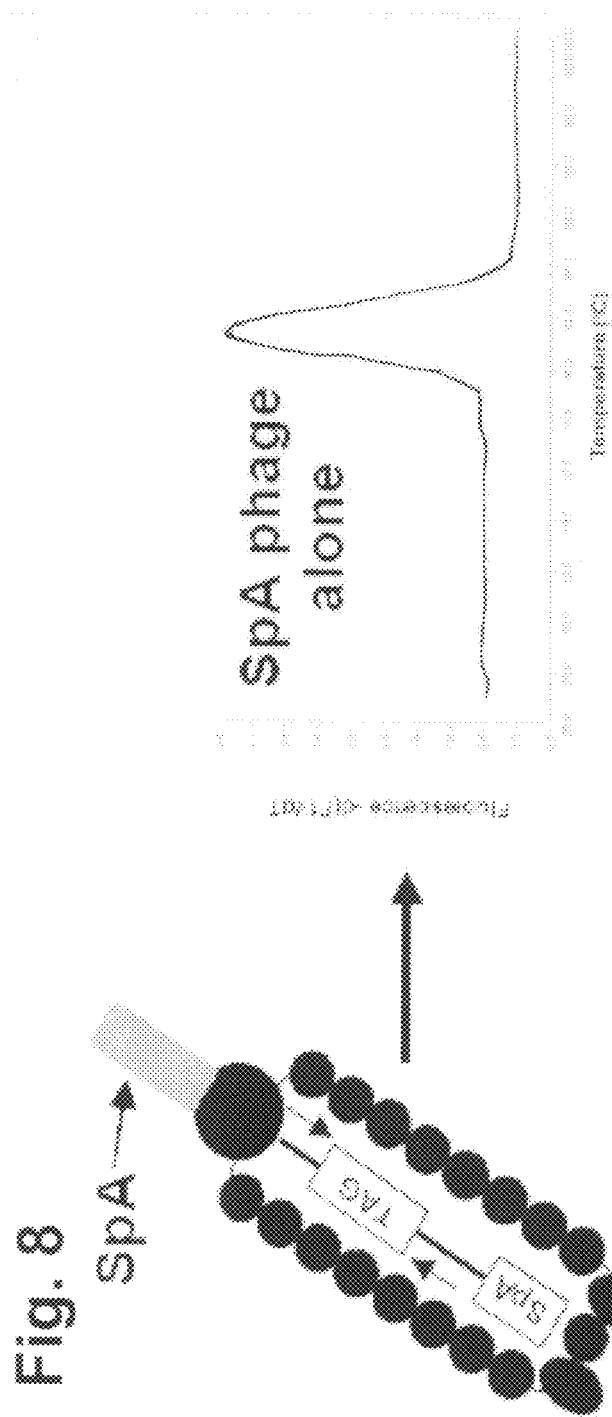

SEQUENCE LISTING

```
<160> NUMBER OF SEQ ID NOS: 8

<210> SEQ ID NO 1
<211> LENGTH: 142
<212> TYPE: DNA
<213> ORGANISM: Artificial sequence
<220> FEATURE:
<223> OTHER INFORMATION: sequence complementary to phage sequence

<400> SEQUENCE: 1
tgctatgtca cttcccttg gttctctcat ctggcctggt gcaataggcc ctgcatgcac      60
tggatgcact ctatcccatt ctgcagcttc ctcattgatg gtctctttta acatttgcat    120
ggctgcttga tgtcccccca ct                                             142

<210> SEQ ID NO 2
<211> LENGTH: 142
<212> TYPE: DNA
<213> ORGANISM: Artificial sequence
<220> FEATURE:
<223> OTHER INFORMATION: sequence complementary to phage sequence

<400> SEQUENCE: 2
tgctatgtca cttcccttg gttctctcat ctggcctggt gcaataggcc ctgcatgcac      60
tggatgcact ctgttttacc tcattatcct tctgccagcg ctagctttta acatttgcat    120
ggctgcttga tgtcccccca ct                                             142

<210> SEQ ID NO 3
<211> LENGTH: 27
<212> TYPE: DNA
<213> ORGANISM: Artificial sequence
<220> FEATURE:
<223> OTHER INFORMATION: forward primer for sequence complementary to
      phage sequence
```

```
<400> SEQUENCE: 3
tgctatgtca cttccccttg gttctct                                   27

<210> SEQ ID NO 4
<211> LENGTH: 30
<212> TYPE: DNA
<213> ORGANISM: Artificial sequence
<220> FEATURE:
<223> OTHER INFORMATION: reverse primer for sequence complementary to
      phage sequence

<400> SEQUENCE: 4
agtgggggga catcaagcag ccatgcaaat                                30

<210> SEQ ID NO 5
<211> LENGTH: 45
<212> TYPE: DNA
<213> ORGANISM: Artificial sequence
<220> FEATURE:
<223> OTHER INFORMATION: artificially synthesized beacon sequence

<400> SEQUENCE: 5
gcgagcatcc cattctgcag cttcctcatt gatggtctcg ctcgc               45

<210> SEQ ID NO 6
<211> LENGTH: 44
<212> TYPE: DNA
<213> ORGANISM: Artificial sequence
<220> FEATURE:
<223> OTHER INFORMATION: artificially synthesized D-Beacon sequence

<400> SEQUENCE: 6
cgagcgtttt acctcattat ccttctgcca gcgctagcgc tcgc                44

<210> SEQ ID NO 7
<211> LENGTH: 33
<212> TYPE: DNA
<213> ORGANISM: Artificial sequence
<220> FEATURE:
<223> OTHER INFORMATION: artificially synthesized B140 annealing
      sequence

<400> SEQUENCE: 7
atcccattct gcagcttcct cattgatggt ctc                            33

<210> SEQ ID NO 8
<211> LENGTH: 33
<212> TYPE: DNA
<213> ORGANISM: Artificial sequence
<220> FEATURE:
<223> OTHER INFORMATION: artificially synthesized D140 annealing
      sequence

<400> SEQUENCE: 8
gttttacctc attatccttc tgccagcgct agc                            33
```

PHAGE PARTICLE DIAGNOSTIC REAGENTS

CROSS-REFERENCE TO RELATED APPLICATIONS

This application is the U.S. national phase application filed under 35 U.S.C. §371 claiming benefit to International Patent Application No. PCT/US2006/044134, filed on Nov. 14, 2006 and U.S. Provisional Patent Application No. 60/740,440, filed on Nov. 29, 2005, which is entitled to priority under 35 U.S.C. §119(a) each of which application is hereby incorporated herein by reference in its entirety.

STATEMENT REGARDING FEDERALLY SPONSORED RESEARCH OR DEVELOPMENT

This research was supported, in part, by U.S. Government funds (National Institutes of Health Grant Nos. HL 02621, HL 54516, and HL 73533), and therefore the U.S. Government has certain rights in the invention.

BACKGROUND OF THE INVENTION

Each year in the United States alone, hundreds of millions of red blood cell (RBC) antigen typings are performed on donated units of blood and the patients that are to receive them. In addition, equivalent numbers of patient antisera are screened for the presence of pre-existing anti-RBC antibodies, the specificities of which must be identified prior to the selection of compatible blood. The technology used in blood banks for doing these tests is essentially the same as the one demonstrated by Landsteiner over 100 years ago—the agglutination of RBCs by an appropriate antisera. Assay systems of this type are labor intensive and typically require teams of highly-trained medical technologists manually shaking test tubes over magnifying mirrors and assessing agglutination patterns by eye. Consequently, blood banks require significantly more bench technologists per test than any other type of clinical laboratory, as reflected in the 10- to 100-fold greater cost per test for the transfusion laboratory than those for other areas of laboratory medicine. In addition, blood donation facilities, blood banks, and hospital transfusion services across the country are facing a growing shortage of skilled staff to perform such tests due to the lack of qualified and interested candidates. This is particularly concerning given the extraordinary importance of accurate pre-transfusion testing and the ability to provide blood components to patients in a timely, often emergent, basis.

As opposed to other forms of laboratory testing such as those in clinical chemistry, coagulation, and hematology, blood bank testing has defied the development of rapid, high-throughput automation. The methods for blood bank automation that are currently available require, in essence, the use of a machine that detects the agglutination of red cells, but agglutination (or some variant thereof) is still the end-point much as it was nearly 100 years ago. Reasons for the difficulty in developing truly automated blood typing systems are multiple, but in large part have to do with the need to work with intact cells in order to detect the presence of specific polymorphic molecules on their surfaces. This is in contrast to other laboratory tests that simply count numbers of cells or measure the concentrations of soluble plasma proteins or electrolytes.

While it is true that flow cytometric testing also detects cell-surface phenotype, the indications for such tests do not, in general, require rapid real-time results such as those required in transfusion medicine where the goal is to prevent the transfusion of incompatible blood, often during emergencies such as trauma or unanticipated surgery, where time and accuracy are of the essence. Furthermore, essential differences in the nature of blood bank testing have precluded the development of "point-of-care" testing devices, such as those now available for glucose or electrolyte determinations or for the rapid "on-the-scene" diagnosis of myocardial infarction. The development of novel blood bank testing methods could lead to the development of small, portable devices for pre-transfusion testing that could facilitate "point-of-care" (e.g., battlefield) testing not possible using conventional approaches.

Another significant issue in blood banking testing is the growing unavailability of complete panels of high-quality immunological reagents for typing. Supplies of conventional sources come from donated human polyclonal antisera that are difficult to quality control and are dwindling in supply due to growing ethical concerns regarding the deliberate hyperimmunization of reagent donors. Because immune responses to many blood group antigens are mounted only in humans (who lack the particular antigen) and not in animals (e.g., mice, whose immune systems generally cannot detect the subtle human polymorphisms to which the antisera needs to be directed), efforts to produce monoclonal typing reagents have required the ability to transform human B-cells, which is a very inefficient and expensive endeavor. Therefore, the availability of endless supplies of well-characterized monoclonal RBC antibodies, analogous to those which revolutionized the automation of other immunological-based assays, such as those for endocrinology or infectious diseases, has been problematic in the field of transfusion medicine.

More than 20 million units of blood are collected in the United States annually, with worldwide collections exceeding 40 million units. Blood collection centers (e.g., American Red Cross, hospital-based donor centers), hospitals, and other blood banks and transfusion centers all have on-going needs to type blood quickly and accurately in a high-throughput manner. Small, automated, blood typing instruments would also have "point-of-care" applications in physician offices such as those of obstetricians in which a patient's Rh type needs to be determined in order to properly administer Rh(D)-immune globulin. Each unit of blood that is collected is typed for at least 3 (i.e., A, B, Rh(D)) antigens and often the blood is tested for detection of many more antigens (e.g., Rh(C), Rh(c), Rh(E), Rh(e), K, $Fy^a$, $Fy^b$, M, N, S, s, $Jk^a$, $Jk^b$, and the like).

Upon receipt of units by a blood bank, standards require that each unit be retested for A and B to ensure proper labeling. Each collected unit of blood is separated into red cells, platelets, and plasma in order to treat 3 different patients with different needs. Approximately twice as many patients are typed for A, B, and Rh(D) (and often other antigens) than those who actually receive blood (i.e., cross-match/transfusion ratio is approximately 2). In addition, blood samples are collected every seventy-two hours on hospitalized patients in order to have fresh samples available for cross-matching purposes such that many patients are typed and retyped many times during their hospitalization. Therefore, the number of blood typings performed worldwide annually is in the hundreds of millions of tests.

As noted previously, essentially all methods for RBC typing, whether manual or automated, use agglutination as the endpoint. The disadvantages of manual methods include labor costs, low throughput, and human error. Disadvantages of current automated methods include inability to multiplex testing reactions and relatively low throughput when compared to other laboratory testing. Additionally, significant disadvantages of both current manual and automated methods include their reliance on conventional sources of antisera, which sources are dwindling in supply and can potentially transmit human disease, or the few human or mouse hybridoma-produced antibodies which are difficult and expensive to produce.

In sum, there is a long-felt and acute need for improved blood typing methods and reagents therefore, which will allow the automation of such tests thereby lowering costs, improving efficiency and accuracy, and obviating the need for current difficult to obtain reagents. The present invention meets these needs.

BRIEF SUMMARY OF THE INVENTION

The present invention includes a method of detecting the presence of an antigen-bearing moiety on a cell, comprising providing a bacteriophage, wherein the bacteriophage comprises a detectable marker molecule and displays on its outer surface an antibody known to specifically bind with the antigen-bearing moiety, wherein the antibody is encoded by a nucleic acid, the sequence of which nucleic acid is at least partially known, further wherein the nucleic acid is not contained within said bacteriophage, and contacting a cell with the bacteriophage. The invention further includes denaturing any bacteriophage specifically bound with the cell to release the marker molecule; and detecting the marker molecule, wherein detecting the marker molecule detects the presence of the antigen-bearing moiety on the cell.

In an embodiment, the marker molecule is selected from the group consisting of a marker nucleic acid, a fluorescent molecule, a polypeptide, a lipid, a carbohydrate, a ligand, a receptor, an enzyme, a substrate, and an inorganic molecule.

In an aspect of the invention, a method comprises amplifying said nucleic acid prior to step (d). In another aspect, a method further comprises washing said cell between step (b) and step (c).

In an embodiment, a method of the invention includes a cell that is a red blood cell and an antigen-bearing moiety that is a red blood cell antigen. In an aspect, a red blood cell antigen is selected from the group consisting of A, B, Rh(D), Rh(C), Rh(c), Rh(E), Rh(e), K, k, $Js^a$, $Js^b$, $Kp^a$, $Le^a$, $Le^b$, $Lu^a$, $Lu^b$, $Fy^a$, $Fy^b$, M, N, S, s, $Do^a$, $Do^b$, $Jk^a$, and $Jk^b$.

In an embodiment, a method of the invention includes a white blood cell and an antigen-bearing moiety is selected from the group consisting of a lymphocyte antigen, a monocyte antigen, and a granulocyte antigen. In one aspect, a cell is a platelet and an antigen-bearing moiety is a platelet antigen. In another aspect, a platelet antigen is selected from the group consisting of HPA-1a, HPA-1b, HPA-2a, HPA-2b, HPA-3a, HPA-3b, HPA-4-a, HPA-4-b, HPA-5a, HPA-5b, HPA-6b, HPA-7b, HPA-8b, HPA-9b, HPA-10b, $Gov^a$, and $Gov^b$.

In an embodiment of the invention, a nucleic acid comprises a sequence complementary to a molecular beacon probe. In an aspect, a molecular beacon probe comprises a fluorophore.

In an embodiment, a nucleic acid is amplified using polymerase chain reaction (PCR). In an aspect, the nucleic acid is amplified by transcription using immuno-detection amplified by T7 RNA (IDAT). In another aspect, the marker molecule is a marker nucleic acid. In yet another aspect, marker nucleic acid is detected by assaying the melting temperature of the marker nucleic acid.

The invention includes a kit for detecting the presence of an antigen-bearing moiety on a cell, the kit comprising a bacteriophage, wherein the bacteriophage comprises a detectable marker molecule and displays on its outer surface an antibody known to specifically bind with the antigen-bearing moiety, wherein the antibody is encoded by a nucleic acid, the sequence of which nucleic acid is at least partially known, further wherein the nucleic acid is not contained within the bacteriophage. A kit further comprises an applicator and an instructional material for the use thereof.

The invention includes a method of detecting the presence of an antigen-bearing moiety on a cell, the method comprising the steps of providing a bacteriophage, wherein the bacteriophage comprises at least two marker molecules, wherein the marker molecules are each distinctly detectable and the bacteriophage displays on its outer surface an antibody known to specifically bind with the antigen-bearing moiety, wherein the antibody is encoded by an antibody-encoding nucleic acid, the sequence of which antibody-encoding nucleic acid is at least partially known, further wherein the antibody-encoding nucleic acid is not contained within the bacteriophage. The invention further includes contacting a cell with the bacteriophage, denaturing any bacteriophage specifically bound with the cell to release the marker molecules, and detecting at least one of the marker molecules, wherein detecting the marker molecules detects the presence of the antigen-bearing moiety on the cell.

The invention includes a method of detecting the presence of at least two different antigen-bearing moieties on a cell, the method comprising the steps of providing a first bacteriophage, wherein the first bacteriophage comprises a detectable first marker molecule and displays on its outer surface an antibody known to specifically bind with a first antigen-bearing moiety, wherein the antibody is encoded by a first nucleic acid, the sequence of which first nucleic acid is at least partially known, further wherein the first nucleic acid is not contained within the bacteriophage. The invention further includes providing a second bacteriophage, wherein the second bacteriophage comprises a detectable second marker molecule and displays on its outer surface an antibody known to specifically bind with a second antigen-bearing moiety, wherein the antibody is encoded by a second nucleic acid, the sequence of which second nucleic acid is at least partially known, further wherein the second nucleic acid is not contained within said bacteriophage. The invention further includes contacting the cell with the first bacteriophage, contacting the cell with the second bacteriophage, detecting the binding of the first bacteriophage with the first antigen-bearing moiety by detecting the presence of the first marker molecule, wherein detecting the first marker molecule detects the presence of the first antigen-bearing moiety on the cell, and further, detecting the binding of the second bacteriophage with the second antigen-bearing moiety by detecting the presence of the second marker molecule, wherein detecting the second marker molecule detects the presence of the second antigen-bearing moiety on the cell.

In an aspect of the invention, the first marker molecule is a first marker nucleic acid, and further the second marker molecule is a second marker nucleic acid. In another aspect, the first and second marker nucleic acids are detected by assaying the melting temperatures of the first and the second marker nucleic acids.

The invention includes a method of detecting the presence of an anti-red blood cell antibody in human serum, the method comprising the steps of contacting a human red blood cell expressing at least one human red blood cell antigen on the surface of the cell with the serum, washing the cell to remove any antibody bound non-specifically with the cell, and providing a bacteriophage, wherein bacteriophage comprises detectable marker molecule and displays on its outer surface an anti-humanglobulin reagent, wherein the reagent is encoded by a nucleic acid, the sequence of which nucleic acid is at least partially known, further wherein the nucleic acid is not contained within the bacteriophage. The method further includes contacting the cell with the bacteriophage, washing the cell to remove any bacteriophage bound non-specifically with the cell, denaturing any bacteriophage specifically bound with the cell to release the marker molecule, and detecting the marker molecule, wherein detecting the marker molecule detects the presence of the anti-red blood cell antibody in the serum.

The invention includes method of detecting the presence of an anti-red blood cell antibody in a human, the method comprising the steps of obtaining a red blood cell from the human, washing the cell to remove any antibody bound non-specifically with the cell, and providing a bacteriophage, wherein the bacteriophage comprises a detectable marker molecule and displays on its outer surface an anti-humanglobulin reagent, wherein the reagent is encoded by a nucleic acid, the sequence of which nucleic acid is at least partially known, further wherein the nucleic acid is not contained within the bacteriophage. The method further includes contacting the cell with the bacteriophage, denaturing any the bacteriophage specifically bound with the cell to release the marker molecule, and detecting the marker molecule, wherein detecting the marker molecule detects the presence of the anti-red blood cell antibody in the human.

The invention includes a method of agglutinating cells, the method comprising the steps of providing a mixture comprising a population of cells, wherein at least a portion of s the population of cells comprises an antigen-bearing moiety, providing a bacteriophage, wherein the bacteriophage displays on its outer surface a first antibody known to specifically bind with the antigen-bearing moiety, wherein the first antibody is encoded by a nucleic acid, the sequence of which nucleic acid is at least partially known, further wherein the nucleic acid is not contained within the bacteriophage. In the invention, the first antibody binds to the portion of the cells, causing the bacteriophage to also bind to the portion of the cells, adding to the mixture a second antibody specific for the bacteriophage, wherein binding of the second antibody to bacteriophage bound to the portion of the cells causes the portion of the cells to agglutinate.

The invention includes a method of detecting the presence of an antigen-bearing moiety in a composition, the method comprising the steps of providing a bacteriophage, wherein the bacteriophage comprises a detectable marker molecule and displays on its outer surface an antibody known to specifically bind with the antigen-bearing moiety, wherein the antibody is encoded by a nucleic acid, the sequence of which nucleic acid is at least partially known, further wherein the nucleic acid is not contained within the bacteriophage. The invention further includes contacting the composition with the bacteriophage, and detecting the marker molecule, wherein detecting the marker molecule detects the presence of the antigen-bearing moiety on the cell.

BRIEF DESCRIPTION OF THE DRAWINGS

For the purpose of illustrating the invention, there are depicted in the drawings certain embodiments of the invention. However, the invention is not limited to the precise arrangements and instrumentalities of the embodiments depicted in the drawings.

FIG. 8 is an image depicting a melting curve analysis for the nucleic acid tag used in an IgG detection reagent according to the present invention.

DETAILED DESCRIPTION OF THE INVENTION

Figure 1:
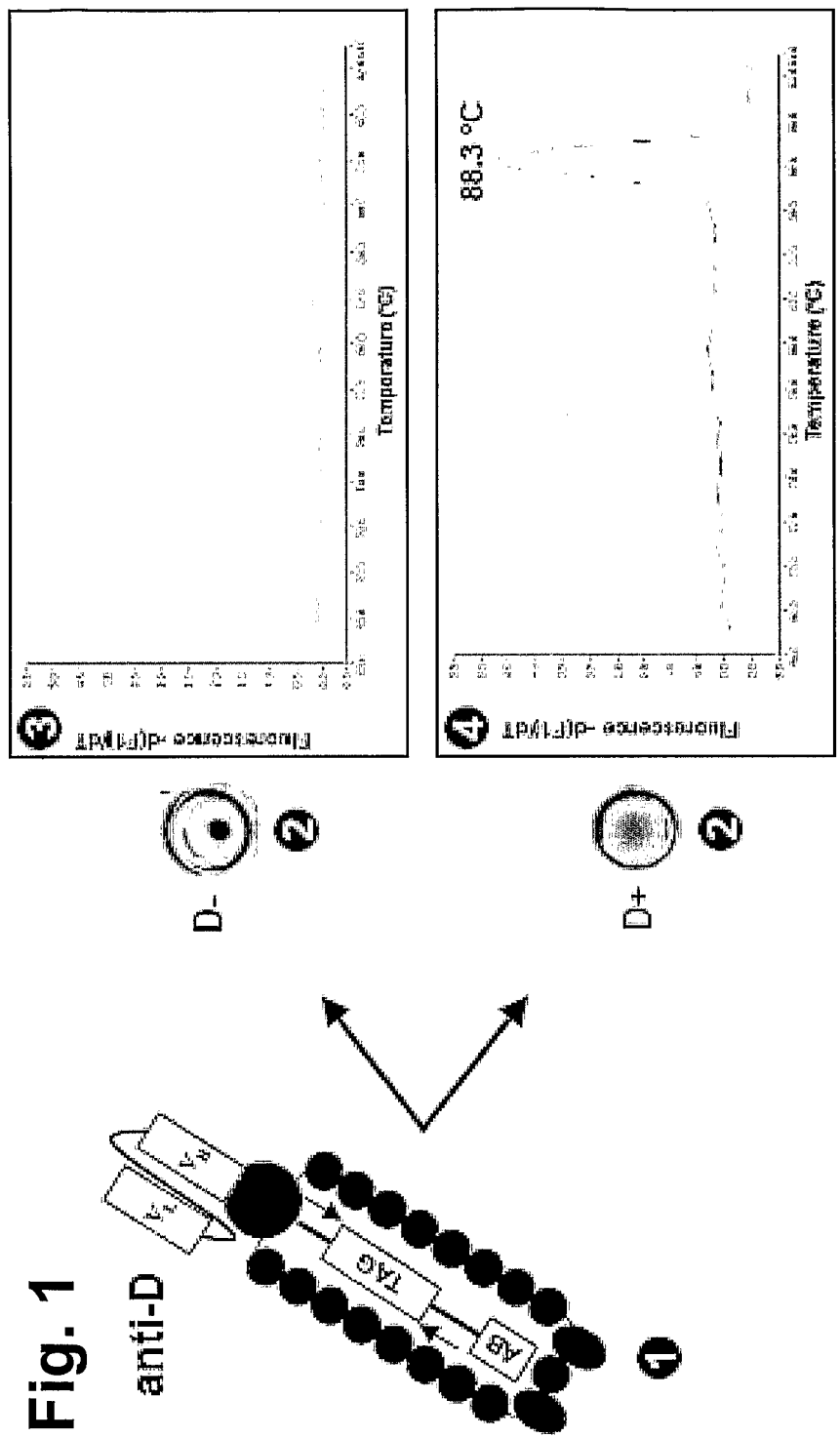
FIG. 1 is a series of images depicting the traditional linkage of phenotype and genotype in phage display technology.

What is currently needed in the art of blood typing is an endless supply of inexpensive anti-RBC reagents that can be used not only in an automated technology, but that are also compatible with conventional manual and automated agglutination methods using anti-M13 antibody as the agglutinating (i.e. "Coombs") agent (e.g., U.S. Pat. No. 5,985,543, to Siegel). The present invention meets these needs and provides, in part, an automated anti-RBC technology that does not rely on conventional phage-display technology.

In particular, the present invention demonstrates that anti-RBC typing methods and reagents can be efficiently and inexpensively used with phage display methods that do not rely upon linking of the phenotype of the RBC with the genotype of the phage. This is because it is shown herein for the first time that a bacteriophage can be produced, wherein the bacteriophage displays one or more antibodies on its outer surface, such as by way of linking an antibody or antibody fragment to a phage coat protein, further wherein the bacteriophage does not contain the nucleic acid encoding the antibody or antibody fragment. In one aspect, the "unlinking" of the phenotype of the RBC from the genotype of the phage, whereas such linking is common in phage display technologies previously known in the art, provides for the use of myriad tagging and detection technologies for the typing of blood using anti-RBC reagents, as described in detail herein.

DEFINITIONS

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

By the term "antigen-bearing moiety" as used herein, is meant a molecule to which an antibody binds. The antigen-bearing moiety may be a membrane bound protein which is selected from the group consisting of an antigen and a receptor. In another aspect, the membrane bound protein is an antigen, such as a red blood cell antigen, such as Rh antigen. When the antigen-bearing moiety is a carbohydrate, it may be a carbohydrate expressed on a glycolipid, for example, a P blood group antigen or other antigen.

As used herein, amino acids are represented by the full name thereof, by the three letter code corresponding thereto, or by the one-letter code corresponding thereto, as indicated in the following table:

| Full Name | Three-Letter Code | One-Letter Code |
| --- | --- | --- |
| Aspartic Acid | Asp | D |
| Glutamic Acid | Glu | E |
| Lysine | Lys | K |
| Arginine | Arg | R |
| Histidine | His | H |
| Tyrosine | Tyr | Y |
| Cysteine | Cys | C |
| Asparagine | Asn | N |
| Glutamine | Gln | Q |
| Serine | Ser | S |
| Threonine | Thr | T |
| Glycine | Gly | G |
| Alanine | Ala | A |
| Valine | Val | V |
| Leucine | Leu | L |
| Isoleucine | Ile | I |
| Methionine | Met | M |
| Proline | Pro | P |
| Phenylalanine | Phe | F |
| Tryptophan | Trp | W |

As used herein, to "alleviate" a disease means reducing the severity of one or more symptoms of the disease.

"Antisense" refers particularly to the nucleic acid sequence of the non-coding strand of a double stranded DNA molecule encoding a protein, or to a sequence which is substantially homologous to the non-coding strand. As defined herein, an antisense sequence is complementary to the sequence of a double stranded DNA molecule encoding a protein. It is not necessary that the antisense sequence be complementary solely to the coding portion of the coding strand of the DNA molecule. The antisense sequence may be complementary to regulatory sequences specified on the coding strand of a DNA molecule encoding a protein, which regulatory sequences control expression of the coding sequences.

The terms "bacteriophage" and "phage" are used interchangeably herein and refer to viruses which infect bacteria. By the use of the terms "bacteriophage library" or "phage library" as used herein, is meant a population of bacterial viruses comprising heterologous DNA, i.e., DNA which is not naturally encoded by the bacterial virus.

By the term "applicator," as the term is used herein, is meant any device including, but not limited to, a hypodermic syringe, a pipette, and the like, for administering the bacteriophage expressing a receptor (e.g., an antiglobulin reagent, an antibody, an anti-antibody, and the like), a cell, a sample, primers, molecular beacon probe, dNTPs, T7 RNA polymerase, and the like, of the invention to a cell, a sample, and the like.

"Biological sample," or simply "sample", as that term is used herein, means a sample, such as one that is, but need not be, obtained from an animal, which sample is to be assessed for the presence of a biological organism, or component thereof, such that the sample can be used to assess the presence, absence and/or level, of an antigen, or ligand, of interest according to the methods of the invention. Such sample includes, but is not limited to, any biological fluid (e.g., blood, lymph, semen, sputum, saliva, phlegm, tears, and the like), fecal matter, a hair sample, a nail sample, a brain sample, a kidney sample, an intestinal tissue sample, a tongue tissue sample, a heart tissue sample, a mammary gland tissue sample, a lung tissue sample, an adipose tissue sample, a muscle tissue sample, and any sample obtained from an animal that can be assayed for the presence or absence of an antigen. Further, the sample can comprise an aqueous sample (e.g., a water sample) however obtained, to be assessed for the presence of an organism, or a component thereof, such as a drinking water sample, before or after any treatment, wherein the presence of a biological organism (e.g., a Cryptosporidium organism) is assessed.

As used herein, the term "fragment" as applied to a nucleic acid, may ordinarily be at least about 20 nucleotides in length, preferably, at least about 30 nucleotides, more typically, from about 40 to about 50 nucleotides, preferably, at least about 50 to about 80 nucleotides, even more preferably, at least about 80 nucleotides to about 90 nucleotides, yet even more preferably, at least about 90 to about 100, even more preferably, at least about 100 nucleotides to about 150 nucleotides, yet even more preferably, at least about 150 to about 200, even more preferably, at least about 200 nucleotides to about 250 nucleotides, yet even more preferably, at least about 250 to about 300, more preferably, from about 300 to about 350 nucleotides, preferably, at least about 350 to about 360 nucleotides, and most preferably, the nucleic acid fragment will be greater than about 365 nucleotides in length.

As used herein, the term "fragment" as applied to a polypeptide, may ordinarily be at least about 20 amino acids in length, preferably, at least about 30 amino acids, more typically, from about 40 to about 50 amino acids, preferably, at least about 50 to about 80 amino acids, even more preferably, at least about 80 amino acids to about 90 amino acids, yet even more preferably, at least about 90 to about 100, even more preferably, at least about 100 amino acids to about 120 amino acids, and most preferably, the amino acid fragment will be greater than about 123 amino acids in length.

By the term "Fab/phage" as used herein, is meant a phage particle which expresses the Fab portion of an antibody.

By the term "scFv/phage" are used herein, is meant a phage particle which expresses the Fv portion of an antibody as a single chain.

"Phage," or "phage particle," as these terms are used herein, include that contain phage nucleic acid encoding, inter alia, an antibody. This is because, as would be appreciated by the skilled artisan, unlike peptide phage display (where the peptide DNA insert is small and it is actually cloned into the phage DNA), the larger scFv or Fab DNA inserts are actually cloned into, among other things, a plasmid. Thus, the nucleic acid encoding the antibody, e.g., a plasmid such as, but not limited to, pComb3, not only comprises a plasmid origin of replication, but also a phage (e.g., M13) origin of replication sequence and an M13 packaging sequence, so that when the nucleic acid is produced, a helper phage can be used to provide the required phage (e.g., M13) proteins in trans to make "phage-like" particles. That is, these particles resemble phage on the outside, but on the inside they contain-plasmid (also referred to as a "phagemid") DNA. In other words, the phagemid DNA need not encode any M13 phage proteins, except a piece of M13 gene III fused to the DNA for antibody or peptide. Thus, it should be understood that the terms "phage," "phage particle," "phage-like particle" and "phagemid" are used interchangeably herein.

A phage is said to "contain" a compound or molecule when the compound or molecule is associated with the interior or the exterior of the phage. For example, a phage is said to contain a nucleic acid if the nucleic acid is located within the phage. Similarly, a phage is said to contain a polypeptide if the polypeptide is fused to a surface coat protein of the phage, thereby displaying the polypeptide on the outer surface of the phage. That is, when a compound or molecule is sequestered inside of a phage particle, or when the compound or molecule is tethered to the outer surface of the phage particle, the compound or molecule is "contained" by the phage, as the compound or molecule cannot freely dissociate from the phage.

A "disease" is a state of health of an animal wherein the animal cannot maintain homeostasis, and wherein if the disease is not ameliorated, then the animal's health continues to deteriorate.

In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

"Homologous" as used herein, refers to the subunit sequence similarity between two polymeric molecules, e.g., between two nucleic acid molecules, e.g., two DNA molecules or two RNA molecules, or between two polypeptide molecules. When a subunit position in both of the two molecules is occupied by the same monomeric subunit, e.g., if a position in each of two DNA molecules is occupied by adenine, then they are homologous at that position. The homology between two sequences is a direct function of the number of matching or homologous positions, e.g., if half (e.g., five positions in a polymer ten subunits in length) of the positions in two compound sequences are homologous then the two sequences are 50% homologous, if 90% of the positions, e.g., 9 of 10, are matched or homologous, the two sequences share 90% homology. By way of example, the DNA sequences 5'ATTGCC3' and 5'TATGGC3' share 50% homology.

"Instructional material," as that term is used herein, includes a publication, a recording, a diagram, or any other medium of expression which can be used to communicate the usefulness of the nucleic acid, peptide, and/or compound of the invention in the kit for detecting the presence of an antigen-bearing moiety on a cell of interest, and/or for detecting an autoantibody in serum. The instructional material of the kit may, for example, be affixed to a container that contains the nucleic acid, peptide, and/or compound of the invention or be shipped together with a container which contains the nucleic acid, peptide, and/or compound. Alternatively, the instructional material may be shipped separately from the container with the intention that the recipient uses the instructional material and the compound cooperatively.

An "isolated nucleic acid" refers to a nucleic acid segment or fragment which has been separated from sequences which flank it in a naturally occurring state, e.g., a DNA fragment which has been removed from the sequences which are normally adjacent to the fragment, e.g., the sequences adjacent to the fragment in a genome in which it naturally occurs. The term also applies to nucleic acids that have been substantially purified from other components that naturally accompany the nucleic acid, e.g., RNA or DNA or proteins, which naturally accompany it in the cell. The term therefore includes, for example, a recombinant DNA which is incorporated into a vector, into an autonomously replicating plasmid or virus, or into the genomic DNA of a prokaryote or eukaryote, or which exists as a separate molecule (e.g., as a cDNA or a genomic or cDNA fragment produced by PCR or restriction enzyme digestion) independent of other sequences. It also includes a recombinant DNA that is part of a hybrid gene encoding additional polypeptide sequence.

"Recombinant polynucleotide" refers to a polynucleotide having sequences that are not naturally joined together. An amplified or assembled recombinant polynucleotide may be included in a suitable vector, and the vector can be used to transform a suitable host cell.

A recombinant polynucleotide may serve a non-coding function (e.g., promoter, origin of replication, ribosome-binding site, etc.) as well.

A host cell that comprises a recombinant polynucleotide is referred to as a "recombinant host cell." A gene that is expressed in a recombinant host cell wherein the gene comprises a recombinant polynucleotide, produces a "recombinant polypeptide."

A "recombinant polypeptide" is one that is produced upon expression of a recombinant polynucleotide.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, adenoviral vectors, adeno-associated virus vectors, retroviral vectors, and the like.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses that incorporate the recombinant polynucleotide.

By describing two polynucleotides as "operably linked" is meant that a single-stranded or double-stranded nucleic acid moiety comprises the two polynucleotides arranged within the nucleic acid moiety in such a manner that at least one of the two polynucleotides is able to exert a physiological effect by which it is characterized upon the other. By way of example, a promoter operably linked to the coding region of a gene is able to promote transcription of the coding region.

Preferably, when the nucleic acid encoding the desired protein further comprises a promoter/regulatory sequence, the promoter/regulatory is positioned at the 5' end of the desired protein coding sequence such that it drives expression of the desired protein in a cell. Together, the nucleic acid encoding the desired protein and its promoter/regulatory sequence comprise a "transgene."

As used herein, the term "promoter/regulatory sequence" means a nucleic acid sequence which is required for expression of a gene product operably linked to the promoter/regulatory sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

A "constitutive" promoter is a nucleotide sequence which, when operably linked with a polynucleotide which encodes or specifies a gene product, causes the gene product to be produced in a living human cell under most or all physiological conditions of the cell.

An "inducible" promoter is a nucleotide sequence which, when operably linked with a polynucleotide which encodes or specifies a gene product, causes the gene product to be produced in a living human cell substantially only when an inducer which corresponds to the promoter is present in the cell.

A "tissue-specific" promoter is a nucleotide sequence which, when operably linked with a polynucleotide which encodes or specifies a gene product, causes the gene product to be produced in a living human cell substantially only if the cell is a cell of the tissue type corresponding to the promoter.

A "polyadenylation sequence" is a polynucleotide sequence which directs the addition of a poly A tail onto a transcribed messenger RNA sequence.

A "polynucleotide" means a single strand or parallel and anti-parallel strands of a nucleic acid. Thus, a polynucleotide may be either a single-stranded or a double-stranded nucleic acid.

The term "nucleic acid" typically refers to large polynucleotides.

The term "oligonucleotide" typically refers to short polynucleotides, generally, no greater than about 50 nucleotides. It will be understood that when a nucleotide sequence is represented by a DNA sequence (i.e., A, T, G, C), this also includes an RNA sequence (i.e., A, U, G, C) in which "U" replaces "T."

In the context of the present invention, the following abbreviations for the commonly occurring nucleic acid bases are used. "A" refers to adenosine, "C" refers to cytidine, "G" refers to guanosine, "T" refers to thymidine, and "U" refers to uridine.

Conventional notation is used herein to describe polynucleotide sequences: the left-hand end of a single-stranded polynucleotide sequence is the 5'-end; the left-hand direction of a double-stranded polynucleotide sequence is referred to as the 5'-direction.

The direction of 5' to 3' addition of nucleotides to nascent RNA transcripts is referred to as the transcription direction. The DNA strand having the same sequence as an mRNA is referred to as the "coding strand"; sequences on the DNA strand which are located 5' to a reference point on the DNA are referred to as "upstream sequences"; sequences on the DNA strand which are 3' to a reference point on the DNA are referred to as "downstream sequences."

A "portion" of a polynucleotide means at least at least about twenty sequential nucleotide residues of the polynucleotide. It is understood that a portion of a polynucleotide may include every nucleotide residue of the polynucleotide.

"Primer" refers to a polynucleotide that is capable of specifically hybridizing to a designated polynucleotide template and providing a point of initiation for synthesis of a complementary polynucleotide. Such synthesis occurs when the polynucleotide primer is placed under conditions in which synthesis is induced, i.e., in the presence of nucleotides, a complementary polynucleotide template, and an agent for polymerization such as DNA polymerase. A primer is typically single-stranded, but may be double-stranded. Primers are typically deoxyribonucleic acids, but a wide variety of synthetic and naturally occurring primers are useful for many applications. A primer is complementary to the template to which it is designed to hybridize to serve as a site for the initiation of synthesis, but need not reflect the exact sequence of the template. In such a case, specific hybridization of the primer to the template depends on the stringency of the hybridization conditions. Primers can be labeled with, e.g., chromogenic, radioactive, or fluorescent moieties and used as detectable moieties.

"Probe" refers to a polynucleotide that is capable of specifically hybridizing to a designated sequence of another polynucleotide. A probe specifically hybridizes to a target complementary polynucleotide, but need not reflect the exact complementary sequence of the template. In such a case, specific hybridization of the probe to the target depends on the stringency of the hybridization conditions. Probes can be labeled with, e.g., chromogenic, radioactive, or fluorescent moieties and used as detectable moieties.

"Recombinant polynucleotide" refers to a polynucleotide having sequences that are not naturally joined together. An amplified or assembled recombinant polynucleotide may be included in a suitable vector, and the vector can be used to transform a suitable host cell.

A recombinant polynucleotide may serve a non-coding function (e.g., promoter, origin of replication, ribosome-binding site, etc.) as well.

A "recombinant polypeptide" is one which is produced upon expression of a recombinant polynucleotide.

"Polypeptide" refers to a polymer composed of amino acid residues, related naturally occurring structural variants, and synthetic non-naturally occurring analogs thereof linked via peptide bonds, related naturally occurring structural variants, and synthetic non-naturally occurring analogs thereof. Synthetic polypeptides can be synthesized, for example, using an automated polypeptide synthesizer.

The term "protein" typically refers to large polypeptides.

The term "peptide" typically refers to short polypeptides.

Conventional notation is used herein to portray polypeptide sequences: the left-hand end of a polypeptide sequence is the amino-terminus; the right-hand end of a polypeptide sequence is the carboxyl-terminus.

As used herein, the term "reporter gene" means a gene, the expression of which can be detected using a known method. By way of example, the *Escherichia coli* lacZ gene may be used as a reporter gene in a medium because expression of the lacZ gene can be detected using known methods by adding a chromogenic substrate, e.g., o-nitrophenyl-β-D-galactopyranoside, to the medium (Gerhardt et al., eds., 1994, Methods for General and Molecular Bacteriology, American Society for Microbiology, Washington, D.C., p. 574).

A "receptor" is a compound that specifically binds with a ligand. This term includes a protein, such as an antibody, an antiglobulin reagent, and the like, that when expressed by a phage and contacted with its cognate ligand, binds specifically therewith.

The term "ligand," as used herein, refers to any protein or proteins that can interact with a receptor binding domain, thus having a "binding affinity" for such domain. Ligands can be soluble or membrane bound, and they can be a naturally occurring protein, or synthetically or recombinantly produced. The "ligand" can also be a nonprotein molecule that acts as ligand when it interacts with the receptor binding domain. Interactions between the ligand and receptor binding domain include, but are not limited to, any covalent or non-covalent interactions. The receptor binding domain is any region of the receptor molecule that interacts directly or indirectly with the ligand.

By the term "specifically binds," as used herein, is meant a molecule, e.g., a protein, a nucleic acid, an antibody, a compound, and the like, which recognizes and binds a specific molecule, but does not substantially recognize or bind other molecules in a sample. For instance, an antibody which recognizes and binds a cognate ligand (i.e., an antigen-bearing moiety present on a cell) in a sample, but does not substantially recognize or bind other molecules in the sample.

To "treat" a disease as the term is used herein, means to reduce the frequency of the disease or disorder reducing the frequency with which a symptom of the one or more symptoms disease or disorder is experienced by an animal.

A "marker," as the term is used herein, refers to a molecule that can be detected. Therefore, a marker according to the present invention includes, but is not limited to, a nucleic acid, a polypeptide, a carbohydrate, a lipid, an inorganic molecule, an organic molecule, or a radiolabel, each of which may vary widely in size and properties. A "marker" can be detected using any means known in the art, or by a previously unknown means that only becomes apparent upon consideration of the marker by the skilled artisan. A marker may be detected using a direct means, or by a method including multiple steps of intermediate processing and/or detection. The term "tag" is also used interchangeably with the term "marker," but the term "tag" may also be used, in certain aspects, to include markers that are associated with one or more other molecules.

As used herein, the term "amplicon" refers generically to a nucleic acid that has been synthesized or amplified using any technique.

As used herein, the term "washing" refers to removing at least one component from a mixture of at least two components. By way of a series of non-limiting examples, salt can be washed from a protein by dialyzing a protein, an antibody can be removed from the outside of a cell by altering the salt conditions of the cell medium or by removing the salt from the cell medium altogether, and an unbound phage can be removed from a cell suspension by separating the cell from the phage using a gel filtration technique.

A nucleic acid is said to "not be contained within a bacteriophage" when the nucleic acid is not present inside the bacteriophage. For example, a nucleic acid sequence, such as an expression vector, is "not contained within a bacteriophage" when the nucleic acid vector is not inserted or incorporated into the interior of the bacteriophage. By way of a non-limiting example, a nucleic acid vector that does not comprise a bacteriophage packaging sequence may not be incorporated into a bacteriophage, whereas a nucleic acid vector that does comprise a bacteriophage packaging sequence may be incorporated into a bacteriophage.

Description

The invention relates to methods for detecting the presence of a molecule of interest on a cell or in a biological sample. Typically, a red blood antigen expressed on a RBC surface is detected, but the invention encompasses detecting the presence of numerous antigens of interest on a wide plethora of cells, including, but not limited to, red and white blood cells, as well as platelets, and cells used for transplantation therapy, and the identification of antigens on cells for forensic purposes (e.g., hair, skin, nail, sperm, saliva, and other cells), among many other uses.

The invention also relates to detection of an antigen of interest in a biological sample. Such a sample includes an aqueous sample to detect the presence of any organism, or component thereof, in the sample.

The invention relates to using an antibody, specific for a known antigen, displayed by a phage (e.g., an M13, T7, lambda, eukaryotic, and the like), to detect the presence of the antigen on a cell or in a biological sample. More specifically, phage specifically bound with a cell are detected by assaying for a specific marker contained by the phage particle. As described in greater detail elsewhere herein, a such marker contained by a phage particle of the invention includes, but is not limited to, a nucleic acid, the sequence of which is at least partially known, a fluorescent marker, a polypeptide, the sequence of which is at least partially known, and the like. Detection of the marker molecule is accomplished using one of many techniques known in the art, thereby detecting the antigen.

The present invention features the incorporation of a pre-determined antibody or antibody particle into a bacteriophage. This is accomplished, in one aspect, by the expression of a fusion protein from a nucleic acid, wherein the fusion protein comprises a bacteriophage coat protein and a pre-determined antibody or antibody fragment. The expressed fusion protein is incorporated into the coat protein assembly of the bacteriophage, and the fusion protein is thereby displayed on the surface of the bacteriophage. Preferably, the nucleic acid encoding the fusion protein is not incorporated into the bacteriophage displaying the fusion protein on its surface. The bacteriophage further comprises at least one marker molecule that can be used to identify the bacteriophage. When a specific marker molecule is incorporated into a bacteriophage displaying a specific fusion protein, as described herein, the marker can also be used to identify the specific fusion protein that is displayed by the bacteriophage. Moreover, knowledge of the antigen that is recognized by the antibody portion of the fusion protein displayed by the bacteriophage allows for the detection of the antigen when the bacteriophage is known to be bound to an antigen-containing sample.

In an embodiment, the invention also features the incorporation of a pre-determined polypeptide into a bacteriophage, wherein the polypeptide is not an antibody or antibody fragment. The invention is useful in this aspect for the incorporation of a non-antibody polypeptide, wherein the polypeptide has an affinity for another molecule, or wherein the polypeptide is known to bind to another molecule. By way of a non-limiting example, such polypeptides include receptor ligands that bind a receptor, receptor fragments that bind a receptor ligand, polypeptides involved in dimerization with a second polypeptide, nucleic acid-binding polypeptides, carbohydrate-binding polypeptides, metal-binding polypeptides, epitopes, and antigens, as well as any fragments thereof that retain some or all of the binding properties of the larger corresponding polypeptide. The compositions and methods used to display an antibody-related polypeptide on the surface of a bacteriophage, wherein the genotype and phenotype of the displaying bacteriophage are unlinked, apply equally to the display of a non-antibody related polypeptide.

Further, the present invention should not be limited to binding of an antigen, eg., a RBC antigen, by an antibody or antibody fragment displayed by a bacteriophage. By way of a non-limiting example, a non-antibody related polypeptide displayed by a bacteriophage may also have affinity for one or more antigens or epitopes displayed by a RBC, and therefore, should be encompassed by the present invention.

Essentially, the marker acts like a tag for detecting an antigen recognized by the antibody displayed by the phage. In this way, the high sensitivity and high throughput screening properties of marker detection methods can be applied to the immunological detection of an antigen, thereby combining the advantages of both technologies. The crucial features of this approach are that the specificity of the antibody displayed by the bacteriophage and the nature and identity of the marker contained by the bacteriophage both be known. It would be understood, based upon the disclosure provided herein, that the precise nature of the antigen, be it a protein, carbohydrate, lipid, or any other compound, recognized by the antibody, need not be known, only that the specificity of the antibody for that antigen be known. For instance, where an antibody is known to bind with and identify a cancer cell (or any cell associated with a disease), but not bind with an otherwise identical cell that is not cancerous (or associated with a disease), the antibody can be used to detect a cancer (or disease state) using the methods of the invention. That is, the antibody binding with a test cell or a biological sample, can be detected by detecting the nucleic acid present in the phage particle encoding the antibody portion, thereby detecting a cancer cell, without having to know the precise nature of the antigen present on the cancer (or disease-associated) cell.

The invention further relates to the ability, for the first time, to prepare a bacteriophage displaying a polypeptide of interest, wherein the bacteriophage comprises at least one marker molecule, wherein the marker molecule is not necessarily linked to the particular polypeptide displayed on the surface of the bacteriophage. That is, a bacteriophage already comprising a specific marker molecule, such as a nucleic acid of known sequence or of particular melting temperature, can be used to produce a bacteriophage displaying a polypeptide of interest. The bacteriophage already comprising a specific marker molecule can also readily be used to produce a bacteriophage displaying a different polypeptide of interest. In one aspect, a benefit provided by the present invention—since the marker molecule does not have to be part of a nucleic acid vector that is transformed into a bacterial cell in conjunction with a bacteriophage—is that a bacteriophage displaying a particular polypeptide and containing a particular marker can be readily prepared, without additional manipulation of the nucleic acid vector encoding the polypeptide of interest. This is because the marker of interest can be incorporated into a bacteriophage prior to the transfection of a bacterial cell and the production of progeny bacteriophage.

The invention further relates to detection of multiple antigens of interest on a cell in a single tube assay. That is, bacteriophage that display antibodies specific for at least two different antigens can be used to detect those antigens on a cell. More specifically, each phage displays an antibody that specifically binds with a known antigen and each phage displays an antibody that recognizes a different antigen, or antigen-moiety. Further, each phage contains a marker molecule, the identity of which is known. In another aspect, each phage contains a multiple marker molecules, the identify of each of which markers is known. Using this approach, the presence of a plurality of antigens of interest can be readily assessed by simply using a panel of phage, each displaying an antibody specific for one of the antigens, where the marker molecule of each phage comprises a known sequence that is distinguishable from that of any other phage in the panel. In this way, multiple antigens can be assayed for using a single reaction step. This "multiplexing" method is not possible using conventional methods that identify the binding of antigen-specific antibodies to a cell since the secondary anti-antibody antibody used to detect the antigen-specific antibodies typically cross-reacts with all the antigen-binding antibodies, or it cannot be determined which antigen-specific antibody the second antibody is bound with. In the case of conventional methods for phenotyping red blood cells, in which antibodies directly agglutinate the appropriate cell type (i.e., no secondary antibody needed), if mixed together, it would likewise not be possible to determine which antigen-specific antibody was responsible for the agglutination. This multiplex approach allows the rapid simultaneous detection of a plurality of antigens using only a single sample.

Further, the invention relates to identification of anti-red blood cell antibodies in serum. That is, a panel of RBCs expressing various known antigens on their surfaces can be contacted with a serum sample. Reagent RBCs expressing characterized antigens are commercially available (e.g., Johnson & Johnson, Raritan, N.J.). The cells are then washed to remove any antibodies non-specifically adhering to the cells and the cells are then contacted with bacteriophage displaying an anti-globulin reagent.

Additionally, autoantibodies present in a patient can be detected by obtaining RBCs from the patient, washing them to remove any antibodies and/or complement that is non-specifically bound with the cells, and the cells can then be contacted with a phage displaying an antihumanglobulin reagent. Thus, by detecting a nucleic acid sequence contained by the phage, the presence of autoantibody on the patient cells, as well as the presence of complement deposited on the cells due to the autoantibody, can be readily detected according to the novel methods disclosed herein.

Conventionally, screening and identification of serum antibodies using reagent red cells displaying known antigens is referred to in the art as an "antiglobulin test", one such test is a Coombs reaction. These assays detect the presence of an antibody, or complement deposited thereby, on a cell of interest. Because complement, while not an antibody, is considered a "globulin", the reagents used to detect antibodies and/or complement are referred to in the art, and also herein, as "antiglobulin" reagents.

These assays, which detect antibodies and/or complement fragments (e.g., C3d) on patient red cells to detect anti-red cell autoantibodies, or the complement they deposit, and also to detect patient alloantibodies, or the complement they deposit, can be used to identify autoantibodies, alloantibodies, or both, that could be destroying autologous cells or transfused cells in a hemolytic transfusion reaction.

As used herein, an "antiglobulin reagent" is a reagent that can detect antibodies, complement, or both. Thus, the present invention includes, as would be understood by one skilled in the art armed with the teachings provided herein, antiglobulin reagents comprising, among others, e.g., anti-antibody antibodies, anti-complement antibodies, Protein A, Protein G, or Protein L, that is, the invention encompasses expression by phage of a wide plethora of reagents that would be understood by the skilled artisan to specifically bind with a globulin, such as antibody, complement, and the like. That is, the present invention includes using an anti-globulin reagent displayed by a phage including, but not limited to, an "anti-antibody antibody," an anti-complement, and any reagent known to bind a globulin (e.g., an antibody, complement, and the like). Additionally, phage displaying Protein A, or an immunoglobulin-binding domain thereof, have been described previously (e.g., Djojonegoro et al., 1994, Bio/Technol. 12:169-172). Such antiglobulin reagent-displaying phage can be used in the methods disclosed herein as would be understood by one skilled in the art armed with the teachings provided herein.

The invention relates to identifying autoantibodies in a serum sample obtained from a patient, or autoantibodies or complement fragments pre-deposited on patient cells in vivo, both characteristics of a disease such as, but not limited to, autoimmune hemolytic anemia. That is, serum obtained from the patient is contacted with an aliquot of reagent RBCs, such as those that are commercially available. RBC autoantibodies bind to common antigens present on essentially all red cells, not just those from the patient. Thus, the patient cannot be transfused with blood from another human since the autoantibodies present in the patient serum with also react with the donor RBCs. Because the patient's RBCs are already coated with the autoantibodies, those autoantibodies already on the cells (i.e., bound to the cells in vivo) can be detected according to the methods of the invention by assaying the cells directly using antihumanglobulin reagent displayed on a phage.

In one aspect, the invention relates to phenotyping a cell with a positive direct antibody typing ("DAT") result. A cell with a positive DAT cannot be typed using a traditional indirect agglutination methods. By way of a non-limiting example, a traditional method of typing a cell sample for a RBC K-antigen would not be successful if the cells in the sample are coated with autoantibody prior to typing. This is because the autologous IgG on the cells will provide a false-positive reading for agglutination. The present invention overcomes this problem, because, for example, adding an "anti-K"-displaying phage particle and developing the reaction with either an anti-M13 agent for agglutination or assaying for an identifying tag within the phage particle (eg., DNA, fluorescent marker), a true positive result will be obtained. This is because, according to the methods and compositions of the present invention, the assay will be unaffected by the presence of autologous IgG on the sample cells.

Alternatively, detecting autoantibodies is performed the same way as is detection of alloantibodies—by contacting the patient serum with reagent red cells. In the case of alloantibodies, only certain reagent RBCs will bind the antibodies, and knowing the precise phenotype of those cells identifies the antigen specificity. In the case of autoantibodies, typically all reagent red cells will bind the antibodies because the autoantigens are present on all cells. Any antibody specifically bound with the RBCs is then detected according to the methods of the invention such as, as more fully disclosed elsewhere herein, by contacting the cells with a phage displaying an antiglobulin reagent and detecting the binding of the phage with the cells by detecting a marker contained by the phage according to the methods of the invention. In this way, autoantibodies present in human serum can be readily detected using the methods disclosed herein analogous to the conventional "indirect antiglobulin test". Furthermore, by contacting patient RBCs with antiglobulin-displaying phage particles and detecting the binding of the phage with the cells by detecting a marker contained by the phage, one can detect the presence of in vivo-deposited autologous antibodies and/or complement fragments on patient RBCs. This assay is analogous to the conventional "direct antiglobulin test," or "DAT."

In one aspect of the present invention, the multiplexing capabilities of the invention enable the DAT process to be completed in a single step, in contrast two the more cumbersome and time-consuming two-step process required by traditional blood typing methods. The present invention therefore increases the speed, efficiency and throughput with which a blood typing reaction can be conducted. Such an increase in efficiency, provided by the present invention, will therefore also reduce the cost as well as the burden of blood typing.

Further, the invention relates to performing compatibility testing between patient serum and red cells drawn from prospective units of blood to be transfused to the patient (i.e., patient/donor "crossmatching"). That is, an aliquot of RBCs from a prospective unit of donor blood can be contacted with a serum sample from a potential transfusion recipient. The cells are then washed to remove any antibodies non-specifically adhering to the cells and the cells are then contacted with bacteriophage displaying an antiglobulin reagent. Thus, the present invention provides methods for detecting an alloantibody in a patient that is to be transfused thereby allowing proper patient/donor crossmatching to prevent incompatible transfusion.

I. Methods

A. Methods of Preparing a Bacteriophage and Detecting an Antigen

The invention includes a method for detecting the presence of an antigen-bearing moiety on a cell. The method comprises contacting a cell with a bacteriophage displaying an antibody that is known to specifically bind with the antigen-bearing moiety when it is present on a cell. Such phage-displayed antibodies, as well as methods for their production, are well-known in the art, and are described in, among others, U.S. Pat. No. 5,876,925, No. 5,985,543, and No. 6,255,455, as well as U.S. patent application Ser. No. 11/074,542, based on International Patent Application PCT/US03/29231 (published as WO 2004/027028) all to Siegel, and all of which are incorporated herein by reference in their entirety. These antibody-displaying bacteriophage are exemplified herein by phage displaying anti-Rh(D) and anti-B specific antibodies. However, the skilled artisan would understand, based upon the disclosure provided herein, that the invention is not limited to these, or any other, particular antibodies displayed on the specific bacteriophage disclosed herein. Rather, the antibody displayed by the phage can be specific for any cell component and techniques for producing phage-displaying antibodies to antigens of interest are well-known in the art, and are encompassed in the present invention.

The procedures for making a bacteriophage library comprising heterologous DNA are well known in the art and are described herein, as well as in for example, in Sambrook et al., supra. Procedures for making a bacteriophage library in which the bacteriophage display a desired protein on the surface are described in detail elsewhere herein.

In one aspect, the invention features a method of making and using a bacteriophage that displays at least one desired polypeptide on the outer surface, yet does not contain a nucleic acid inside the bacteriophage that encodes a polypeptide displayed on the outer surface. Such a bacteriophage is said to have an "un-linked" phenotype and genotype. Methods of making and using such bacteriophage are described in greater detail elsewhere herein.

By way of a non-limiting example, a bacteriophage displaying a polypeptide on the outer surface, but not containing an encoding nucleic acid within, wherein the encoding nucleic acid encodes the polypeptide displayed on the outer surface, can be made by a method comprising the following steps. Such a vector can be a commercially-available vector. A nucleic acid vector is prepared, wherein the vector comprises a nucleic acid sequence encoding an antibody, antibody fragment, or any polypeptide that has an affinity for another molecule, or the ability to bind to one or more other molecules. The vector additionally comprises a nucleic acid sequence encoding a polypeptide that will be directed to and/or displayed on the outer surface of a bacteriophage. Such polypeptides and sequences are known in the art of phage display, as set forth elsewhere herein, and will therefore not be discussed in detail herein. In one embodiment, the nucleic acid sequence is an M13 gene III sequence.

In another embodiment of the invention, the nucleic acid sequence encoding the displayed polypeptide is adjacent to the nucleic acid sequence encoding a binding polypeptide. In one aspect, the two nucleic acid sequences are fused to one another. In yet another aspect, the two nucleic acid sequences are joined to one another by a nucleic acid linker sequence of one or more nucleotides. By way of a non-limiting example, a nucleic acid sequence encoding an M13 gene III polypeptide is fused to a nucleotide sequence encoding a scFv antibody fragment, such that an M13 gene III protein—scFv fusion protein can be expressed and subsequently, displayed on the outer surface of a bacteriophage.

The nucleic acid vector is inserted into a bacterial cell, using any methods now known in the art, or any methods later discovered. A "helper phage" is also used to transfect the same bacterial cell, either before, concomitant with, or after insertion of the nucleic acid vector into the bacterial cell. Helper phage useful in the present invention are discussed in detail elsewhere herein. By way of a non-limiting example, such phage include M13 helper phage.

Therefore, in one embodiment, the invention features a method of preparing a phage-displayed antibody or antibody fragment, wherein the nucleic acid encoding the antibody or antibody fragment is not contained by the bacteriophage. By way of a non-limiting example, a nucleic acid encoding an antibody can be fused to a nucleic acid encoding the M13 gene III coat protein of a bacteriophage. The fusion nucleic acid is inserted into a nucleic acid vector, using techniques known to the skilled artisan. This plasmid construct, which does not contain an M13 bacteriophage packaging sequence, is then transformed into a bacterial cell for the production of antibody-gene III coat protein fusion protein. M13 bacteriophage is then added to the bacterial cell. When the bacteriophage directs the production of additional phage particles, the antibody-gene III coat protein fusion protein is incorporated into the coat protein structure of the progeny bacteriophage. However, the plasmid construct encoding the antibody-gene III coat protein fusion protein will not be packaged into the progeny bacteriophage, because the plasmid construct lacks the appropriate packaging sequence. The progeny bacteriophage display the antibody on their outer surface, but do not contain within the bacteriophage the nucleic acid sequence encoding the antibody, thus—as set forth for the first time herein—resulting in an antibody-displaying bacteriophage having an "un-linked" phenotype and genotype.

Accordingly, bacteriophage which display a desired antibody can be engineered such that the antibody protein is displayed on the surface thereof in such a manner that it is available for binding to its corresponding binding protein, e.g., the antigen against which the antibody is directed. Thus, when bacteriophage which display a specific antibody are incubated in the presence of a cell which expresses the corresponding antigen, the bacteriophage will bind to the cell. Bacteriophage which do not display the antibody will not bind to the cell. Such panning techniques are well known in the art and are described for example, in Wright et al. (supra).

Processes such as those described above, have been developed for the production of human antibodies using M13 bacteriophage display (Burton et al., 1994, Adv. Immunol. 57:191-280). Methods relating to production of such display libraries, and the screening thereof, are set forth in U.S. Pat. No. 6,255,455, to Siegel, which is incorporated by reference as if set forth in its entirety herein. The present invention provides additional methods of producing bacteriophage that display such antibodies, wherein the DNA encoding a displayed antibody is not contained within a bacteriophage displaying the antibody.

In one aspect of the invention, a cDNA library is generated from mRNA obtained from a population of antibody-producing cells. The mRNA encodes rearranged immunoglobulin genes and thus, the cDNA encodes the same. Amplified cDNA is cloned into expression vectors or phagemids that do not contain M13 packaging signals, wherein the cDNA is cloned in-frame with a bacteriophage coat protein to produce a contiguous nucleic acid that encodes an antibody-coat protein fusion protein. When the expression vectors or phagemids are co-transformed into a bacterial cell with a bacteriophage, the expression of the antibody fusion protein allows for the incorporation of the antibody/coat protein fusion protein into the phage particles produced, thereby creating a library of phage which display human Fab (or scFv) fragments on their surface. Phage which display the antibody of interest can be selected by antigen binding.

Although the bacteriophage displaying antibodies of interest herein are exemplified by M13 phage, the present invention is not limited to these, or any other, vector displaying an antibody. Instead, one skilled in the art would appreciate, when armed with the teachings provided herein, that any vector that can display an antibody can be used in the methods disclosed herein. Therefore, while the antibody-displaying bacteriophage disclosed herein are exemplified by M13, other bacteriophage, such as lambda phage or T7 phage, can also be useful in the method of the invention. Lambda phage display libraries have been generated which display peptides encoded by heterologous DNA on their surface (Sternberg et al., 1995, Proc. Natl. Acad. Sci. USA 92:1609-1613) as have T7 phage display libraries (Hansen et al., 2001, Int. J. Oncol. 19:1303-1309).

Moreover, it is contemplated that the method of the invention may be extended to include viruses other than bacteriophage, such as eukaryotic viruses. In fact, eukaryotic viruses can be generated which encode genes suitable for delivery to a mammal and which display an antibody capable of targeting a specific cell type or tissue into which the gene is to be delivered. For example, retroviral vectors have been generated which display functional antibody fragments (Russell et al., 1993, Nucl. Acids Res. 21:1081-1085). These, and any other vector expressing an antibody can be used in the methods of the invention and are encompassed thereby.

Furthermore, while the method of the invention as exemplified herein describes using phage which encode the Fab portion or an scFv portion of an antibody molecule, the method should not be construed to be limited solely to the use of phage encoding Fab or scFv antibodies. Fab molecules comprise the entire Ig light chain, that is, they comprise both the variable and constant region of the light chain, but include only the variable region and first constant region domain (CH1) of the heavy chain. Single chain antibody molecules comprise a single chain of protein comprising the Ig Fv fragment. An Ig Fv fragment includes only the variable regions of the heavy and light chains of the antibody, having no constant region contained therein. Phage libraries comprising scFv DNA may be generated following the procedures described in Marks et al., 1991, J. Mol. Biol. 222:581-597, or using the methods set forth in detail herein. Panning of phage so generated for the isolation of a desired antibody is conducted as described herein for phage libraries comprising Fab DNA.

The invention should also be construed to include synthetic phage display libraries in which the heavy and light chain variable regions may be synthesized such that they include nearly all possible specificities. Therefore, antibody-displaying libraries can be "natural" or "synthetic" (Barbas, 1995, Nature Medicine 1:837-839; de Kruif et al., 1995, J. Mol. Biol. 248:97-105). Antibody-displaying libraries comprising "natural" antibodies are generated as described in, e.g., U.S. Pat. No. 5,876,925, to Siegel. Antibody-displaying libraries comprising "synthetic" antibodies are generated following the procedure described in Barbas (1995, supra) and the references cited therein.

The skilled artisan would appreciate, based upon the disclosure provided herein, that the red blood cell antibodies to which antibodies can be generated using methods known in the art and can then be used in the method of the invention include, but are not limited to, Rh antigens, including Rh(D), Rh(C), Rh(c), Rh(E), Rh(e), and other non-Rh antigens, including red blood cell antigens in the Kell, Duffy, Lutheran and Kidd blood groups.

Thus, the method of the invention can be used for detection of any RBC antigen or other cell antigen, such as, but not limited to, tumor-specific antigen, bacterial antigens, and the like. The method of the invention is also useful for typing platelets by generating phage antibodies specific for a number of clinically important platelet antigens, notably, HPA-1a/1b, HPA-2a/2b, HPA-3a/3b, and the like.

The invention is further useful for typing donor white blood cells for HLA antigens for the purposes of matching donors and recipients for potential transplant matching in the case of both solid (for example, kidney, heart, liver, lung) and non-solid (for example, bone marrow) organ or tissue transplanting.

In addition, the methods of the present invention can be used for forensic purposes, to detect any antigen of interest in a sample, where the sample can be, but is not limited to, bone, hair, skin, semen, saliva, or any other sample that can be obtained from an organism or biological sample. The only feature required is that the sample contain an antigen that can be specifically recognized by an antibody displayed by a bacteriophage, or other antibody-displaying vector. Thus, the present invention is not limited in any way to the detection of any particular antigen; instead, the invention encompasses detecting a wide plethora of antigens of interest using the detection methods disclosed herein.

Thus, the invention encompasses detecting an antigen of interest on a red blood cell, referred to herein as "phenotyping," by detecting the binding of a phage displaying an anti-red blood cell antibody, where the phage is detected by detecting a known marker contained by the phage particle. Further, the invention includes screening of patient sera for anti-red blood cell antibodies using phage particles that display anti-human IgG (or anti-IgM or anti-kappa/lambda light chain antibody which would pick up any Ig isotype). Again, the phage bound with the RBCs is detected by detecting a marker contained by the phage.

Additionally, the invention encompasses using a method as set forth herein in an immune assay, whether the antigen being detected is on a cell or not (e.g., antigens such as, but not limited to, any measured for research or clinical purposes from a cytokine to HCG for a pregnancy test). That is, the present invention combines the specificity conferred by immunoglobulins for a given substance, which specificity takes into account any post-translational modification (e.g., phosphorylation, glycosylation, and the like), with the sensitivity conferred by marker detection methods—as well as the ability to perform multiplex assays. That is, a sample being assayed would be applied such that its components are affixed to a solid support, such as coating the well of a plate for an ELISA, nitrocellulose filter, bead, or any other solid support, and the phage expressing a protein that specifically binds with a cognate ligand can be allowed to bind with the components affixed to the solid support. Any phage specifically bound to a cognate ligand can be detected by detecting a known marker contained within or on the phage. Thus, the presence of any ligand of interest can be detected using the methods disclosed herein even where the sample being assayed does not comprise a cell.

Moreover, the skilled artisan would appreciate, based upon the disclosure provided herein, that the invention encompasses the phenotyping of other blood cells (e.g., platelets, white cells, and the like) and the detection of antibodies to those cells in the blood (e.g., anti-platelet auto- or alloantibodies, anti-HLA antibodies, etc.), such that the present invention is not limited to red blood cells. Indeed, the invention is not limited to blood cells at all, but can be used to detect any molecule of interest present on any kind of cell. Thus, one skilled in the art would appreciate, based upon the disclosure provided herein, that the present invention includes, but is not limited to, detecting a molecule of interest on a cell where flow cytometry would otherwise be used such that the wide plethora of antibodies now available (e.g., hundreds of anti-CD antibodies, such as anti-CD4 or CD-8 for helper/suppressor T cells, anti-CD20 for B cells, and the like) can be displayed on a phage and used to detect, according to the novel methods disclosed elsewhere herein, whether the antigen is present in a cell. The present invention includes using antibodies to be developed in the future to antigens of interest as these are developed and used according to the methods disclosed herein.

The skilled artisan would appreciate, based upon the teachings provided herein, that detection of any molecule of interest, for instance, with regard to forensic application of the methods disclosed herein, provides an important advantage over present methods in that many antigens important for identifying the origin of fluids (blood or soluble substances in saliva, and the like) are carbohydrates (like the A and B antigens). Using genetic testing on the miniscule spot for DNA cannot identify carbohydrate-modified proteins, because DNA does not encode carbohydrates. Rather, carbohydrates are products of post-translational modification of proteins. Prior art methods relating to carbohydrate detection are limited to detecting the DNA for the enzymes (e.g., the glycosytransferases) that are responsible for assembling the sugar moieties onto the protein or lipid. The problem with conventional detection assays is that the ultimate expression of a particular sugar is the result of the inheritance of a number of enzymes that act in precise sequence to assemble the chains such that the genes for all of the enzymes would need to be detected in order to identify the identity of the person the sample was derived from. For example, in order for an individual to be blood group A, the enzyme that adds N-acetylgalactosamine onto its precursor sugar is required, as is the enzyme (a fucosyl transferase) to assemble the precursor sugar. Other carbohydrates (like P) are even more complicated in their structures and assembly. If the sample comprises a mixture of secretions in one spot from different individuals, DNA testing would pick up all enzymes and the test would not be able to distinguish whether one person had all the enzymes and could make a particular sugar antigen or if the sample comprised DNA from various persons who could each only produce the various sugar components. Unlike conventional nucleic acid-based testing, the present invention provides the advantage of combining the exquisite specificity of an antibody that is capable of recognizing a complex structure, such as a glycan, and the ability to detect miniscule quantities of a nucleic acid; thus, detection of the marker contained by the phage, combined with the specificity of an antibody, provide a novel assay with the extraordinary sensitivity and specificity required in forensic uses.

One skilled in the art, based upon the disclosure provided herein, would understand that while the term "phenotyping" is generally used in the art to detecting a characteristic demonstrated by a cell or organism, the term relates to the identification of any antigen of interest, whether or not the antigen is associated with a cell, by detecting a known marker. Thus, for instance, the identification of a drug in a dried spot on a car door using a phage-displayed anti-drug antibody according to the methods of the invention, would be "phenotyping" as the term is used herein. Therefore, the methods of the invention, where an antibody expressed by a phage binds with a cognate antigen and the antigen is detected by assaying for a marker contained by the phage, is "phenotyping" as used herein.

Indeed, the skilled artisan, armed with the teachings provided herein, would realize that the present invention is not limited to detection of an "antigen" using phage-displayed antibody (which antibody is then detected by detecting a marker contained by the phage). Instead, the present invention encompasses using a non-antibody protein expressed by a phage, which protein specifically binds with a cognate ligand present on a cell, in a sample, or both. Many such binding pairs are well-known in the art and have been identified using a wide variety of assays, including yeast two- and three-hybrid binding assays, among a wide plethora of other assays. Thus, where a binding pair is known in the art, one of the two molecules can be expressed by the phage (the binding pair protein expressed by the phage is referred to herein as the "receptor") and the presence of the other member of the binding pair (referred to as the "ligand" or "target") can be detected by detecting a marker contained by the phage displaying the receptor protein. The ligand that is to be detected by its cognate receptor/binding partner displayed by the phage can include, but is not limited to, a hormone, or a portion of a hormone where the portion can bind with the receptor displayed by the phage. Further, the methods of the present invention can be used to, inter alia, measure the expression of a hormone receptor on a cell by assessing the amount of a phage displaying the hormone, or portion thereof, which binds with the cell being assayed. The phage specifically bound with the cell due to the receptor/ligand (hormone receptor/hormone expressed by the phage, respectively) interaction can be detected by detecting a marker contained by the phage as more fully disclosed elsewhere herein.

One skilled in the art would understand, based upon the disclosure provided herein, that the present invention encompasses detection of a molecule of interest that is not associated with a cell. That is, the present invention includes assaying for the presence of a molecule of interest in any sample where the sample can be applied to a solid support such that the molecule of interest can be immobilized. A phage displaying an receptor known to bind specifically with that molecule (herein referred to as a "ligand" or "target" molecule) can then be contacted with the immobilized sample and the binding of any phage can be detected by assaying for the presence of a marker contained by the phage as more fully described elsewhere wherein. In this way, the present invention can be used to detect a molecule of interest (ligand) present in any sample using the methods disclosed herein.

The skilled artisan would also appreciate, based upon the disclosure provided herein, that a phage can readily expresses a peptide that is known to detect cancer cells but where it is not known what component on the cancer cell the peptide binds with. Thus, the protein known to bind cancer cells can be used to detect a cancer cell even though the identity of the ligand/binding partner that binds with the protein is not known, by detecting bound phage by detecting a marker contained by the phage, all as more fully disclosed elsewhere herein.

Additionally, where the phage is used to detect the binding of serum antibodies to a reagent red blood cell, the phage can express Staph Protein A, or a portion thereof, instead of anti-IgG, to detect immunoglobulins bound with the RBCs. Therefore, the skilled artisan would appreciate, based upon the disclosure provided herein, that a wide plethora of molecules can be displayed by the phage to detect a cognate binding partner present on a cell, in a tissue or aqueous sample, and the like, and the present invention is not in any way limited to phage displaying an antibody, or to detection of an antigen on a cell, as exemplified elsewhere herein. That is, once a binding pair is known, the skilled artisan, armed with the disclosure provided herein, would readily be able to detect one of the binding pair using the methods of the invention, i.e., by displaying one member of the binding pair on a phage and contacting the phage with a sample, then detecting any phage specifically bound with the sample by detecting a marker contained by the phage. This allows the rapid and sensitive detection of a molecule of interest, or various molecules of interest where multiplexing is used, where the molecule is not a nucleic acid, by detecting a pre-determined marker.

The specific conditions under which the antibody, or receptor, displayed by the bacteriophage is allowed to specifically bind with an antigen, or ligand, of interest will depend on the specific antigen-antibody and/or receptor-ligand complex involved in the reaction. The skilled artisan would understand, based upon the disclosure provided herein, that such conditions can be readily determined for each antigen/binding pair being detected and the antibody/receptor being used to do so, as is exemplified herein for detection of Rh(D) and B antigens on intact red blood cells using phage displaying antibodies specific for these antigens. These techniques for determining binding conditions are routinely practiced in the art, and are therefore not described further herein.

Once the bacteriophage displaying the antibody (or receptor) are specifically bound with the cell, or ligand in a sample, via the interaction between the antigen-bearing moiety on a molecule of interest present on the cell (ligand) and the antibody displayed by the phage (receptor), the presence of bound phage is detected by detecting the marker contained by the bacteriophage particle. For the M13 phage set forth herein, the marker can be, for example, a nucleic acid that is a single-stranded DNA molecule, but the present invention is not limited to any particular nucleic acid; rather, any nucleic acid can be detected using techniques well-known in the art (e.g., as described in Sambrook et al., 1989, Molecular Cloning: A Laboratory Manual, Cold Spring Harbor Laboratory, New York; and Ausubel et al., 1997, Current Protocols in Molecular Biology, John Wiley & Sons, New York), some of which are disclosed herein, as well as techniques to be developed in the future, and these various techniques are all encompassed in the invention.

Other markers useful in the present invention include, but are not limited to, a fluorescent molecule, or any spectrophotometrically-detectable molecule, such as a molecule detectable using magnetic resonance techniques (i.e., "spin labels"), a radiolabeled molecule (i.e., a molecule including C, H, and/or O isotopes), a chemically-reactive molecule (i.e., a molecule containing one or more amino groups or sulfhydryl groups), or molecule containing one or more groups detectable by affinity chemistry (i.e., ligand-receptor or enzyme-substrate technologies).

In yet another embodiment of the invention, a marker includes a polypeptide. A peptide useful in the invention includes a polypeptide that is distinguishable from a native bacteriophage polypeptide, including any non-native peptide (eg., mammalian). Such polypeptides may be introduced into a bacteriophage by transforming an expression vector comprising the polypeptide into the bacterial cell infected with bacteriophage. Expression of the non-native polypeptide provides a ready supply of polypeptide for incorporation into the bacteriophage. The polypeptide may be incorporated into the bacteriophage using one of many methods known to the skilled artisan, including, but not limited to, fusion of the non-native polypeptide to another polypeptide that has an affinity for a bacteriophage polypeptide, polynucleotide, or receptor. In this embodiment, the non-native polypeptide will become incorporated into the bacteriophage as a result of the fusion of the non-native polypeptide to another polypeptide that is typically incorporated into a bacteriophage. In one aspect of the invention, a non-native polypeptide may be introduced into a bacteriophage by transforming an expression vector comprising a non-native polypeptide/bacteriophage gene III coat protein fusion protein into a bacterial cell infected with bacteriophage. The non-native polypeptide/bacteriophage gene III coat protein fusion protein is expressed in the infected bacteria, and the entire fusion protein is incorporated into the coat protein assembly of the bacteriophage.

Other bacteriophage coat proteins useful in the invention include, but are not limited to, the gene VIII coat protein. As will be understood by the skilled artisan when armed with the disclosure set forth herein, the non-native polypeptide may be present either on the inside of the bacteriophage, or it may be displayed on the outside of the bacteriophage, depending upon the nature of the fusion protein construct, as will be understood by one of skill in the art. Further, the non-native polypeptide may be "fused" to a coat protein, such as the gene VIII coat protein, or to the shaft of the coat protein.

The present invention also encompasses methods of amplifying markers used in bacteriophage according to a method of the invention. For example, as will be understood by the skilled artisan when armed with the present disclosure, a fluorescent molecule used as a marker may be amplified through interaction with a second marker molecule, or alternatively, with a non-marker molecule.

In yet another embodiment, a marker molecule of the present invention further comprises two or more molecules that collectively operate as a signaling moiety. For example, one molecule in the signaling moiety is a fluorescent molecule such as a ReAsH molecule, a bis-((N-iodoacetyl)peperazinyl)sulfonerhodamine (BSR) molecule, a Cy3B molecule, a Cy5 molecule, or a fluorescein molecule. The second molecule is a fluorescent molecule, such as a ReAsH molecule, a bis-((N-iodoacetyl)peperazinyl)sulfonerhodamine (BSR) molecule, a Cy3B molecule, a Cy5 molecule, or a fluorescein molecule. Third and additional molecules can be a ReAsH molecule, a bis-((N-iodoacetyl)peperazinyl)sulfonerhodamine (BSR) molecule, a Cy3B molecule, a Cy5 molecule, or a fluorescein molecule. Preferably, the signaling moiety comprises two fluorescent molecules, such as a fluorescein molecule and a BSR molecule or a fluorescein molecule and a Cy3B molecule. Thus, as demonstrated by the present disclosure, a marker molecule of the present invention can comprise any combination of molecules that are capable of generating a fluorescent or polarity signal detectable by one of the methods disclosed elsewhere herein and known in the art. In addition, the present invention can comprise the use of two or more molecules that generate a detectable fluorescent or polarity signal supplemented with additional fluorescent- or polarity-generating molecules that are capable of amplifying the detectable fluorescent or polarity molecules. Such interactions can be detected using any useful method know in the art, including, but not limited to fluorescent energy resonance transfer (FRET).

The present invention also encompasses amplification of a marker nucleic acid to assist in its detection. However, the present invention is not limited to methods requiring the amplification of the nucleic acid. Instead, the skilled artisan, based upon the disclosure provided herein, would appreciate that detection methods which do not require amplification of the nucleic acid are encompassed in the invention. Such detection methods include, but are not limited to, detection of a nucleic acid directly transferred to a chip wherein a fluorescent (or enzyme)-labeled Qligonucleotide complementary to the phage(mid) sequence can detect the unamplified nucleic acid.

The skilled artisan would understand, once armed with the teachings provided herein, that, as exemplified herein, a marker nucleic acid can be amplified using conventional polymerase chain reaction assays. The production of PCR primers, and probes that hybridize with the sequence amplified by the PCR, are well-known in the art, and these methods are described in, among others, Sambrook et al. (1989, Molecular Cloning: A Laboratory Manual, Cold Spring Harbor Laboratory, New York), and Ausubel et al. (1997, Current Protocols in Molecular Biology, John Wiley & Sons, New York). That is, a set of primer sequences can be developed based on the known sequence of the nucleic acid contained by the bacteriophage. As discussed elsewhere herein, the primers can be specific for any portion of the nucleic acid, or any other sequence present in the nucleic acid. Detection of a marker, such as an amplified nucleic acid, indicates the presence of the antigen recognized by the specific antibody displayed by the bacteriophage. Other PCR-based DNA assays useful in the present invention include, but are not limited to, detection of DNA using PCR melting curves, as described in U.S. Patent Application Publication No. 2005-0136399 A1 of Siegel (U.S. patent application Ser. No. 10/971,933), which is hereby incorporated herein by reference in its entirety A marker, or "tag" nucleic acid of the invention can be derived from any source, including, but not limited to, an isolated, naturally-produced nucleic acid, a nucleic acid fragment of a larger nucleic acid of either a natural or synthetic source, a fully-synthetic nucleic acid, or an isolated naturally-occurring nucleic acid that has been modified by any means, including any in vitro or in vivo means. Therefore, a marker or "tag" nucleic acid of the present invention can be any nucleic acid from any source, and the sequence of such a nucleic acid may be fully known, partially known, or completely unknown. As will be understood by the skilled artisan based on the disclosure set forth herein, a nucleic acid can be useful in the present invention, regardless of how much information is known about the sequence of such a nucleic acid.

In one aspect of the invention, a marker nucleic acid, such as a phage reagent DNA, can be detected by PCR amplification and amplicon melting point analysis. In one embodiment, by carrying out PCR amplification in the presence of a dye that fluoresces when bound to double-stranded DNA, fluorescent amplicons can be generated. If the temperature of an amplicon-containing mixture is lowered, then slowly raised, amplicon fluorescence will fall off at the characteristic melting temperature for that particular amplicon. The melting temperature will be a function of both amplicon length and G:C/A:T content, and will act as a "signature" for that particular tag. The types of fluorescent compounds useful in this aspect of the invention are known in the art, and therefore, will not be discussed in detail herein.

In another embodiment of the invention, as set forth in greater detail elsewhere herein, phage particles containing nucleotide tags of differing length, flanked by an identical pair of PCR primer annealing sites, are simultaneously amplified and subsequently differentiated by their amplicon melting points. As will be understood based on the disclosure set forth herein, the length of a nucleotide tag of the invention will govern the unique "signature" melting temperature at which the tag melts in PCR-based analysis. The determination of an optimal or desired length of nucleotide tag, as well as the particular sequence of the tag, is therefore within the skill in the art. Additional methods of determining melting points of nucleic acids, now known or later discovered, will be understood by the skilled artisan to be encompassed by the present invention, and are equally useful in the present invention.

Additionally, the skilled artisan would appreciate, based upon the disclosure provided herein, that sequences can be inserted into a marker nucleic acid, which inserted sequence can then be detected using various assays known in the art. For instance, as discussed elsewhere herein, "molecular beacons", or as used herein, "beacons" or "beacon sequences," are stem-and-loop-structured oligonucleotides with a fluorescent label at the 5' end and a universal quencher at the 3' end (see, e.g., Tyagi and Kramer, 1996, Nature Biotech. 14:303-308; Broude, 2002, Trends in Biotechnology 20:249-256). When the stem is closed (in the absence of complementary nucleic acid), the fluorophore and quencher are in close proximity and fluorescent energy is absorbed by the quencher and fluorescence is quenched and not detectable. In the presence of complementary nucleic acid, the loop of the beacon hybridizes and the fluorophore and quencher separate such that quenching does not occur. Photons are then emitted from the fluorophore, unquenched, at the wavelength specific for that fluorophore and fluorescence is then detectable. By combining a number of beacons in one tube, each with a different fluorophore at their 5' ends, multiple DNA (Tyagi et al, 1998, Nature Biotech. 16:49-53) or RNA (de Baar et al., 2001, J. Clin. Microbiol. 39:1895-1902) targets can be simultaneously detected by measuring the spectrum of colors emitted from the reaction vessel.

Molecular beacons of two, or more, different colors can be incorporated into a PCR and/or a transcription reaction (e.g. IDAT) to detect the presence of a marker DNA. As described elsewhere herein, the marker nucleic acid of each bacteriophage, can be modified to insert a unique beacon sequence and each molecular beacon probe can be conjugated to a unique quencher/fluorophore pair such that each beacon, when bound with its complementary sequence, will fluoresce at a unique frequency. In this way, each beacon can be used to detect an antibody binding with an antigen such that the "multiplex" reaction can yield results demonstrating which antigens are present on a cell being examined by assessing which fluorophores are present in the sample. The design and production of such "beacon" sequences, and nucleic acid sequences comprising sequences complementary thereto, are well known in the art.

Armed with the disclosure provided herein, the skilled artisan would understand that the present invention is not limited in the number of molecules of interest that can be detected in a single multiplex reaction. That is, the design of unique markers that can be detected and distinguished from the each other in a single reaction is well-known in the art. Further, one skilled in the art would appreciate, based upon the disclosure provided herein, that various technologies, such as, but not limited to, microchip arrays, slot blots, use of beacon probes, and other high-throughput assays allowing the processing of many samples, and providing the capability for multiplex assays, can be used in the methods of the present invention as exemplified herein, as known in the art, or using techniques to be developed in the future, the use of which can be readily contemplated based upon the disclosure provided herein. That is, current chip technology already provides that the number of antigens that can be assayed on a single chip exceeds the number of known red blood cell antigens. Further, where the cycling parameters of various PCR reactions are compatible, a single tube comprising numerous primer pairs can be used to multiplex the PCR reactions. Thus, multiplexing the reactions relating to the methods of the invention would appear to only be limited as to the number of spots on the chips, since the binding of phage to cells, the number of primers that can be used perform PCR in a single tube, and the like, do not limit the number molecules that can be assayed for using the methods of the invention.

B. Detection of Multiple Antigens

The present invention encompasses a method for detecting the presence of at least two different antigen-bearing moieties on a cell. The method comprises contacting at least two different bacteriophage, each displaying an antibody that specifically binds an antigen, and each containing a unique marker, where the two antibodies do not bind the same antigen. Any phage that are non-specifically bound with the cell are removed (e.g., by washing the cell), and the presence of any bound bacteriophage is detected by detecting the marker contained by the phage, as more fully described elsewhere herein. Because each bacteriophage comprises a marker that is distinguishable from those present in other bacteriophages present in the same sample, the presence of various antigens can be detected in a single sample mixture. Such "multiplex" assays are not possible using antibody-based detection methods, since the reagents used to detect the presence of antibodies bound with the cell cannot readily distinguish between each antibody. Further, conventional blood typing does not use reagents that detect the presence of antibodies bound with the cell since many blood typing reagents, typically the decavalent IgMs, directly agglutinate the cells. In those assays, one cannot multiplex the reaction it would not be possible to determine which reagent caused the agglutination. However, methods based on detecting multiple, unique markers, make assaying for various antigens, by detecting the markers contained by phage particles bound to/linked with those antigens via an antibody molecule expressed by the phage, possible as demonstrated herein.

One skilled in the art would appreciate, based upon the disclosure provided herein, that the various bacteriophage, each displaying a different antibody recognizing an antigen distinct from the antigens recognized by any other phage-displayed antibody present in the sample, can be contacted with the cell being assayed simultaneously, in the same reaction mixture. However, the bacteriophage can be contacted with the cell in serial fashion, such that each bacteriophage contacted with the cell, any unbound bacteriophage is removed, and the next bacteriophage can be contacted with the cell, the unbound phage removed, and on and on, until all of the bacteriophage have been allowed to bind with the cell such that all of the antigens of interest have been assayed for on the cell. All the bound phage can then be treated to release the marker contained by the bacteriophage, and the various markers present in the sample can be detected as discussed more fully elsewhere herein. Because each bacteriophage expressing a unique antibody contains a marker of known identity that is distinct from the markers contained by all the other bacteriophage used in the assay, the binding of each bacteriophage can be determined separately from all the others. Thus, the presence of each antigen assayed for can be determined by detecting the unique marker associated with the bacteriophage displaying the antibody that bound with that antigen because detecting various markers in a sample does not interfere with the detection of other, unrelated, markers in that same sample.

The skilled artisan would appreciate, based upon the disclosure provided herein, that where speed is desired, different antigens can be assayed for in a single reaction mixture. Moreover, where greater sensitivity of the assay is desired, e.g., where forensic detection of a small sample is involved, or where the particular combination of phage required for the assay are somehow incompatible with the same amplification scheme or conditions, then the various reactions can be performed serially. By way of a non-limiting example, in the case of a nucleic acid marker, while it is preferred that PCR be performed by adding all the relevant primers into one tube and amplifying all the fragments at once, the invention also encompasses methods where each antigen/ligand is identified in serial fashion using the same sample. In designing the primers and the stretches of phage (or phagemid) DNA to amplify, it is therefore preferable to design specific sequences (tags) to be amplified in the phage DNA, since such sequences can be made compatible in terms of multiplexing and cycling conditions. As exemplified herein for detection of B and Rh(D) antigens on an RBC using anti-B and anti-Rh(D) displayed by phage, the primers can be designed to be used in a single reaction and the phage are added together to the RBCs and the PCR is performed in a single tube to produce corresponding amplicons. As will further be understood by the skilled artisan, the invention is not limited to this particular scheme.

Therefore, a number of different phage-displayed antibodies (e.g., antibodies specific for various blood group antigens) can be contacted simultaneously with a sample of RBCs. The unbound phage are removed, and the markers contained by the phage bound with the cells are assayed to determine which phage bound with the cells. Since each bacteriophage contains a unique marker, appropriate methods can be used to determine which phage, and therefore, which antigens, are present on the cells. As will be understood by the skilled artisan, an appropriate method for marker detection will be employed (i.e., PCR detection for nucleic acid markers, fluorescent spectrometric detection for fluorescent markers, antibody-based detection for polypeptide markers, etc. . . . ). This "multiplex" method is a vast improvement over prior art methods which require that each antigen be assayed for separately, thereby requiring additional reagents, increasing the technical difficulty and length of the assay, and introducing more opportunity for errors in requiring additional steps and manipulations.

Additionally, a number of different phage-displayed blood group antibodies can be contacted simultaneously to the same sample of red cells and the differences in antibody markers can be exploited to determine which ones bound and which ones did not, as demonstrated herein using anti B and anti-Rh(D) antibodies displayed on different phage. Such "multiplexing" is not possible by agglutination methods as one could never tell which antibody(ies) caused the agglutination.

The skilled artisan, based upon the disclosure provided herein, would readily appreciate that such "multiplexing" strategy is not limited to any particular antibodies, but can be used to detect multiple red blood cell antigens using a wide plethora of antibody-displaying phage, where each phage comprises a marker that can be detectably distinguished from the markers contained by phage displaying antibodies having different specificities, or even phage displaying antibodies having the same specificities, so long as the markers of the phage can be distinguished from one another. Indeed, these methods are not limited to red blood cells or their antigens, but can be readily applied to any system where it is desirable to detect the presence of multiple antigens on a cell, or in a sample.

C. Detection of Antibody in Serum

The present invention includes a method for detecting the presence of autoantibodies or alloantibodies in serum, more specifically, for detecting anti-red blood cell antibodies present in human serum (indirect antiglobulin test). The method comprises contacting a human red blood cell expressing at least one red blood cell antigen with a serum sample to be assayed. The cell is washed to remove non-specifically bound antibodies and the cell is then contacted with bacteriophage displaying an antiglobulin reagent on its surface. Where there is a human antibody (IgG, IgM, and the like) bound with the cell, the bacteriophage will bind via the antiglobulin reagent displayed by the phage. The presence of phage specifically bound with the cell (via binding with the human antibody on the cell) can then be detected as disclosed herein based on detection of a known marker contained by the bacteriophage. In another embodiment of the invention, a second washing step is used to remove unbound anti-globulin phage regarding prior to detection of the known marker.

In this way, where the antigen composition of a panel of cells is known, this reference panel of cells can be used to assay for the presence of antibodies to these antigens in any sample by simply and rapidly detecting the marker contained by a bacteriophage displaying an antiglobulin on its surface, to increase the efficiency and sensitivity, as well as to automate, assays that were previously performed using antibody-based detection methods.

D. Detection of Antibody or Complement Fragments on Red Blood Cells

The present invention includes a method for detecting the presence of autoantibodies, alloantibodies, or complement fragments bound to the surface of red blood cells, more specifically, for the diagnosis of autoimmune hemolytic anemia or for the determination of alloimmune destruction of transfused red blood cells (direct antiglobulin test). The method comprises washing a sample of red blood cells to remove non-specifically bound antibodies and then contacting the cells with bacteriophage displaying an antiglobulin reagent on its surface. Where there is human antibody or complement bound with the cell, the bacteriophage will bind via the antiglobulin reagent displayed by the phage. The presence of phage specifically bound with the cell (via binding with the human antibody or complement on the cell) can then be detected as disclosed herein based on detection of a marker contained by the bacteriophage. In this way, the present invention can be used to increase the efficiency and sensitivity, as well as to automate, assays that were previously performed using antibody-based detection methods.

E. Performing Donor/Recipient Compatibility Testing

The present invention includes a method for assuring compatibility, i.e., non-reactivity, between antibodies in patient sera and an aliquot of red blood cells drawn from a unit of blood intended for transfusion (crossmatching). The method comprises contacting a sample of characterized donor red blood cells with a patient serum sample to be tested. The cells are washed to remove non-specifically bound antibodies and the cell is then contacted with bacteriophage displaying an antiglobulin reagent on its surface. Where there is human antibody bound with the cell, such as would be the case with an incompatible crossmatch, the bacteriophage will bind via the antiglobulin reagent displayed by the phage. The presence of phage specifically bound with the cell (via binding with the human antibody on the cell) can then be detected as disclosed herein based on detection of a marker contained by the bacteriophage. In this way, the present invention can be used to increase the efficiency and sensitivity, as well as to automate, assays that were previously performed using antibody-based detection methods.

II. Kits

The invention includes various kits which comprise a compound, such as a bacteriophage displaying an antibody with known specificity for an antigen of interest, a primer pair for amplifying a known nucleic acid sequence present in the phage, a molecular beacon for detecting a known sequence present in the nucleic acid contained by the bacteriophage, a reagent for use in an IDAT reaction (e.g., T7 RNA polymerase, DNA polymerase I, dNTPs, and the like), and/or compositions of the invention, an applicator, and instructional materials which describe use of the compound to perform the methods of the invention, and any combination of the preceding components. Although exemplary kits are described below, the contents of other useful kits will be apparent to the skilled artisan in light of the present disclosure. Each of these kits is included within the invention.

In one aspect, the invention includes a kit for detecting the presence of an antigen-bearing moiety on a cell. The kit is used pursuant to the methods disclosed in the invention. Briefly, the kit may be used to contact a bacteriophage displaying an antibody that specifically binds with the antigen-bearing moiety when it is present on a cell. This is because, as more fully disclosed elsewhere herein, binding of the bacteriophage with the cell, and subsequent detection of a marker contained by the phage, indicates that the phage bound with the cell, thereby indicating that the antibody displayed by the phage bound with its cognate antigen, thus, in turn, indicating that the antigen is present on the cell.

The kit further comprises an applicator useful for administering the bacteriophage, PCR primers, molecular beacons, and the like, to a sample. The particular applicator included in the kit will depend on, e.g., the method used to detect the antigen as disclosed herein, and such applicators are well-known in the art and may include, among other things, a pipette, a syringe, a dropper, and the like. Moreover, the kit comprises an instructional material for the use of the kit. These instructions simply embody the disclosure provided herein.

In one aspect, the kit further comprises a bacteriophage expressing an antibody that specifically binds a red blood cell antigen, such as, but not limited to, RBC antigens A, B, Rh(D), Rh(C), Rh(c), Rh(E), Rh(e), K, $Fy^a$, $Fy^b$, M, N, S, s, $Jk^a$, $Jk^b$.

Further, in another aspect, the kit further comprises a molecular beacon. These sequences are contained within the nucleic acid contained by the bacteriophage such that sequences hybridizing therewith can detect the presence of phage (or phagemid) nucleic acid. In yet another aspect, the kit comprises a PCR primer than can amplify the nucleic acid sequence present in the phage.

The kit also includes a pharmaceutically-acceptable carrier. The composition is provided in an appropriate amount as set forth elsewhere herein.

Additional kits, such as those for detecting complement, and auto- and allo-antibodies in a sample, as well as kits for detecting any ligand of interest where a known ligand/receptor binding pair is known, are also included as would be readily appreciated by one skilled in the art based upon the disclosure provided herein.

The invention is now described with reference to the following Examples. These Examples are provided for the purpose of illustration only and the invention should in no way be construed as being limited to these Examples, but rather should be construed to encompass any and all variations which become evident as a result of the teaching provided herein.

EXAMPLES

Experimental Example 1

Phage Reagent DNA can be Detected by PCR Amplification and Amplicon Melting Point Analysis By carrying out PCR amplification in the presence of a dye that fluoresces when bound to double-stranded DNA, fluorescent amplicons can be generated. If the temperature is lowered, then slowly raised, amplicon fluorescence will fall off at the characteristic melting temperature for that amplicon. The melting temperature will be a function of both amplicon length and G:C/A:T content.

Similarly, as set forth in detail herein, phage particles containing nucleotide tags of differing length, flanked by an identical pair of PCR primer annealing sites, were simultaneously amplified and subsequently differentiated by their amplicon melting points.

Figure 10:
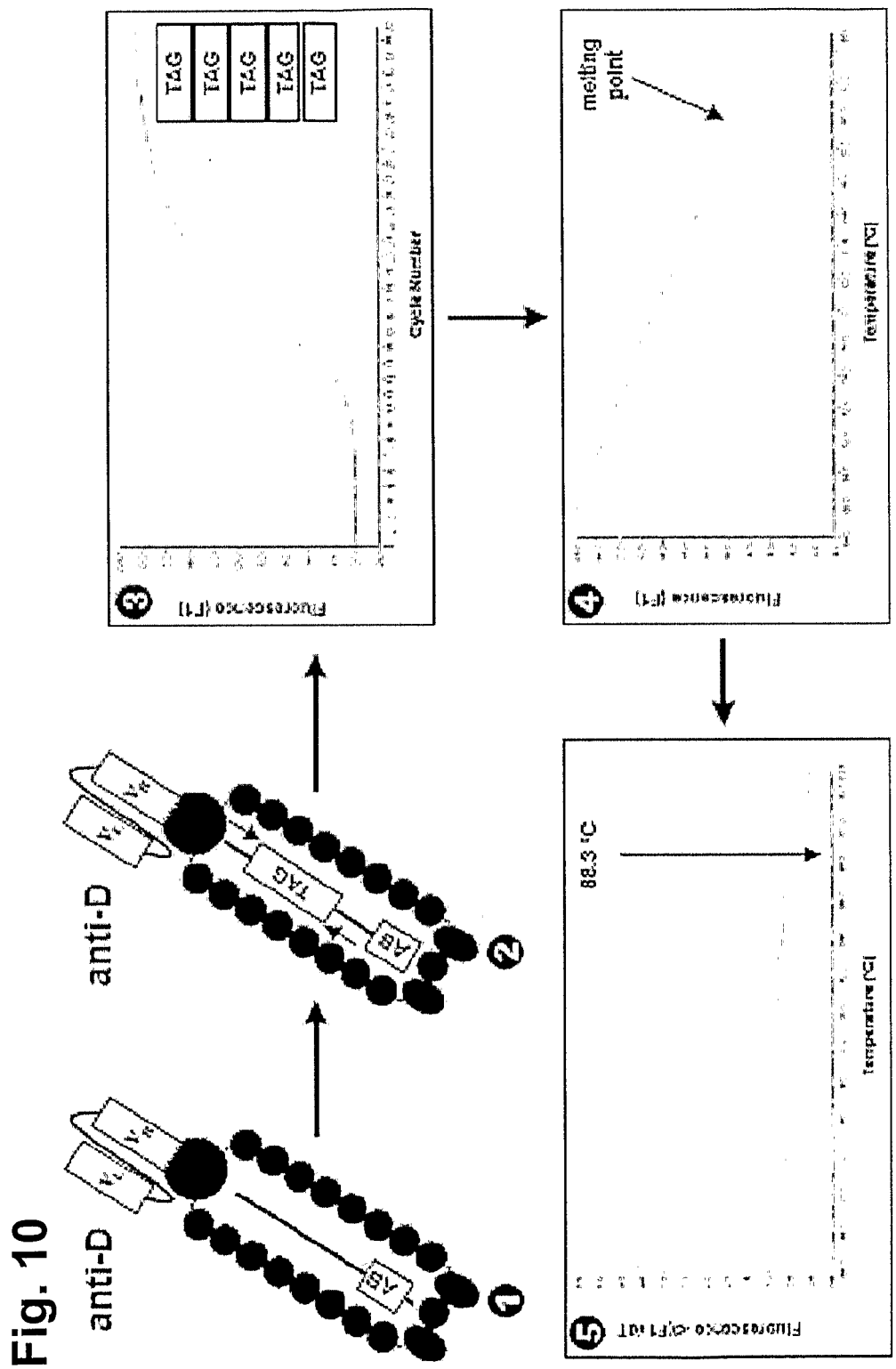
FIG. 10 is a series of images depicting the utility of amplicon melting point analysis in detection of phage reagent DNA.

An M13 filamentous phage particle expressing a human anti-Rh(D) (i.e. Rhesus(D)) mAb derived from previous studies using the pComb3X phage display system (clone E1M2) was used for developing this assay. As described in detail elsewhere herein, the DNA within the anti-Rh(D)-displaying phage particle contains the antibody heavy and light chain variable region sequences that encode the displayed antibody (FIG. 10). Using the NotI restriction site located down-stream from the antibody cloning site in a non-coding region of the pComb3X phagemid, a 58-bp piece of random DNA was inserted ("TAG", FIG. 10). PCR amplification using upstream and downstream oligonucleotide primers (arrows in FIG. 10) were designed to yield a 146-bp amplicon. When PCR was carried out in the presence of SYBR Green, a dye that fluoresces when bound to double-stranded DNA, the generation of amplicons could be followed using a Lightcycler II (Roche Diagnostics) real-time PCR instrument. PCR cycles were rapid, comprising 10 sec for annealing, 5 seconds for extension, and 10 seconds for denaturing steps. Following PCR, the temperature of the reagent mix was lowered to 65° C., then raised 0.1° C./sec. to 95° C. The fluorescent signal began to fall off as amplicons melted (FIG. 10). Plotting the negative first derivative of this curve revealed the precise melting point temperature (88.3° C.) of the tag (FIG. 10). Subsequent experiments revealed sensitivities in the detection of this anti-Rh(D) reagent to a low as <100 antibody molecules.

These results demonstrate that exploiting the presence of nucleic acid within a phage particle can be used to develop an extraordinarily sensitive readout for the presence of a reagent, a sensitivity that in fact rivals radioisotope labeling.

Experimental Example 2

Phage Reagent Products with "Unlinked" Genotype and Phenotype

To test the ability to multiplex typing reactions with phage-displayed anti-RBC antibodies, an anti-RBC antibody-expressing phage particle to an additional RBC antigen than Rh(D) and with a different length tag than the Rh(D) reagent described above would be needed. Before creating one, a novel method was devised and tested for making phage reagents that would offer a number of advantages over those used previously. As illustrated in FIG. 1, traditional phage-displayed antibodies link the phenotype of an antibody with its genotype—i.e., the phage contain the nucleotide sequence of the displayed antibody within the particle. This is the hallmark of phage display in that it enables the creation of libraries of phage from immune repertoires, as well as the selection of specific "binders" by panning against an antigen, and that it allows the captured, antigen-specific phage to replicate themselves in E. coli cultures. The ability of phage-displayed antibodies to direct their own replication is thus important in the antibody discovery process, but not important for the use and utility of actual anti-RBC phage reagents. In fact, in some circumstances, it may be undesirable if end-users are able to regenerate reagents by infecting their own E. coli cultures with a traditional self-replicating phage reagent. Therefore, the present invention sets forth a novel method by which phage reagents are generated, wherein the phage reagents do not contain antibody sequences inside, but in fact display anti-RBC antibodies on the outside ("copy-protected" particles). A second advantage of such an approach is that the identity of the nucleic acid, and therefore, polypeptide sequence of the displayed antibody is protected, as it is not readily available to the end-user of the phage particle.

Figure 2:
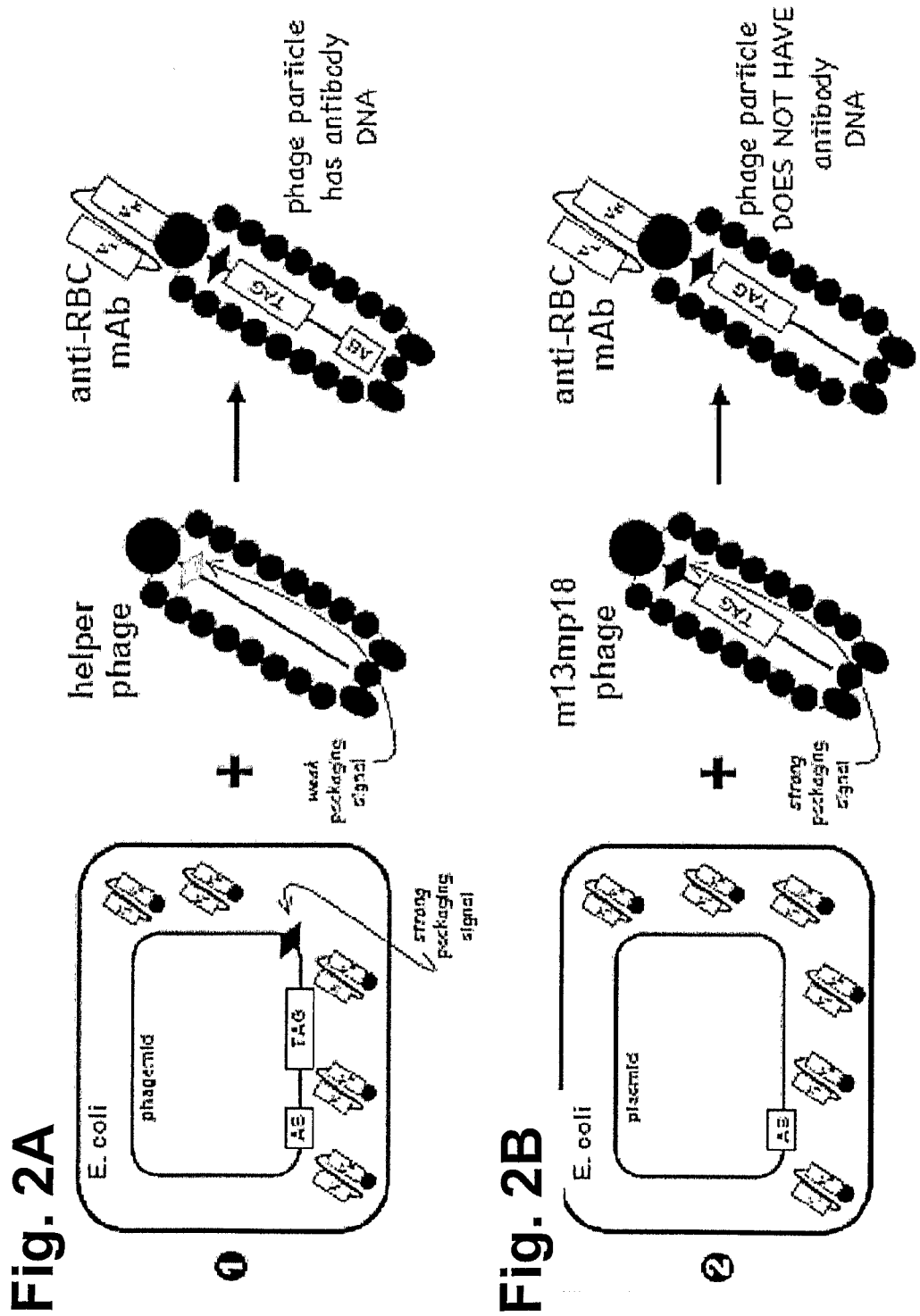
FIG. 2A is a series of images depicting the incorporation of an antibody-encoding phagemid into a phage based on a strong packaging sequence.
FIG. 2B is a series of images depicting the lack of incorporation of an antibody-encoding plasmid into a phage when the plasmid does not contain a packaging sequence.

As illustrated in FIG. 2A, antibody and tag sequences are contained within a phagemid that produces antibody in E. coli. The antibody is actually produced as a fusion protein with the pIII coat protein of M13, which is the reason why the antibody eventually becomes expressed on the phage particle surface. One of the reasons the DNA containing the antibody and tag sequences is called a "phagemid" rather than a "plasmid" is that a phagemid contains the DNA packaging signal for M13 phage particle assembly. Upon co-infection with "helper phage", a commercially available form of M13 phage that has a weakened packaging signal in its genome, phage particles are produced that contain the phagemid rather than the helper phage DNA.

In order to produce "copy-protected" particles, as described above, the antibody sequence was first removed from the phagemid vector and placed into a generic plasmid that produced the antibody/pIII fusion protein in E. coli (FIG. 2B). Then, by co-infecting the culture with M13 phage containing a normal wild-type packing signal, phage particles were produced containing the wild-type M13 genomic DNA, but not the antibody-containing DNA. Also shown in FIG. 2B, a detection tag can also be incorporated into the phage used for co-infection, as described in greater detail elsewhere herein. One advantage of this method of production of phage reagent particles is that when a phage-displayed antibodies is sought to be produced having a different tag for a specific purpose, the time-consuming cloning of one or more different specific tag nucleic acid sequences into each different phagemid antibody DNA is not required, since the tag comes from the generic phage. For example, m13 mp18 phage is illustrated in FIG. 2B, as it is M13 phage with a multiple cloning site that would facilitate the introduction of DNA tags of choice.

In practice, it is possible to keep frozen stocks of E. coli containing phagemid DNA with a particular antibody sequence. To make a batch of phage reagent with a desired DNA tag, an aliquot of frozen stock is grown in culture, co-infected with the desired tag-containing m13 mp18 phage, and thereby, "copy-protected", "tagged" phage reagents can be harvested from the culture supernatant.

Figure 3:
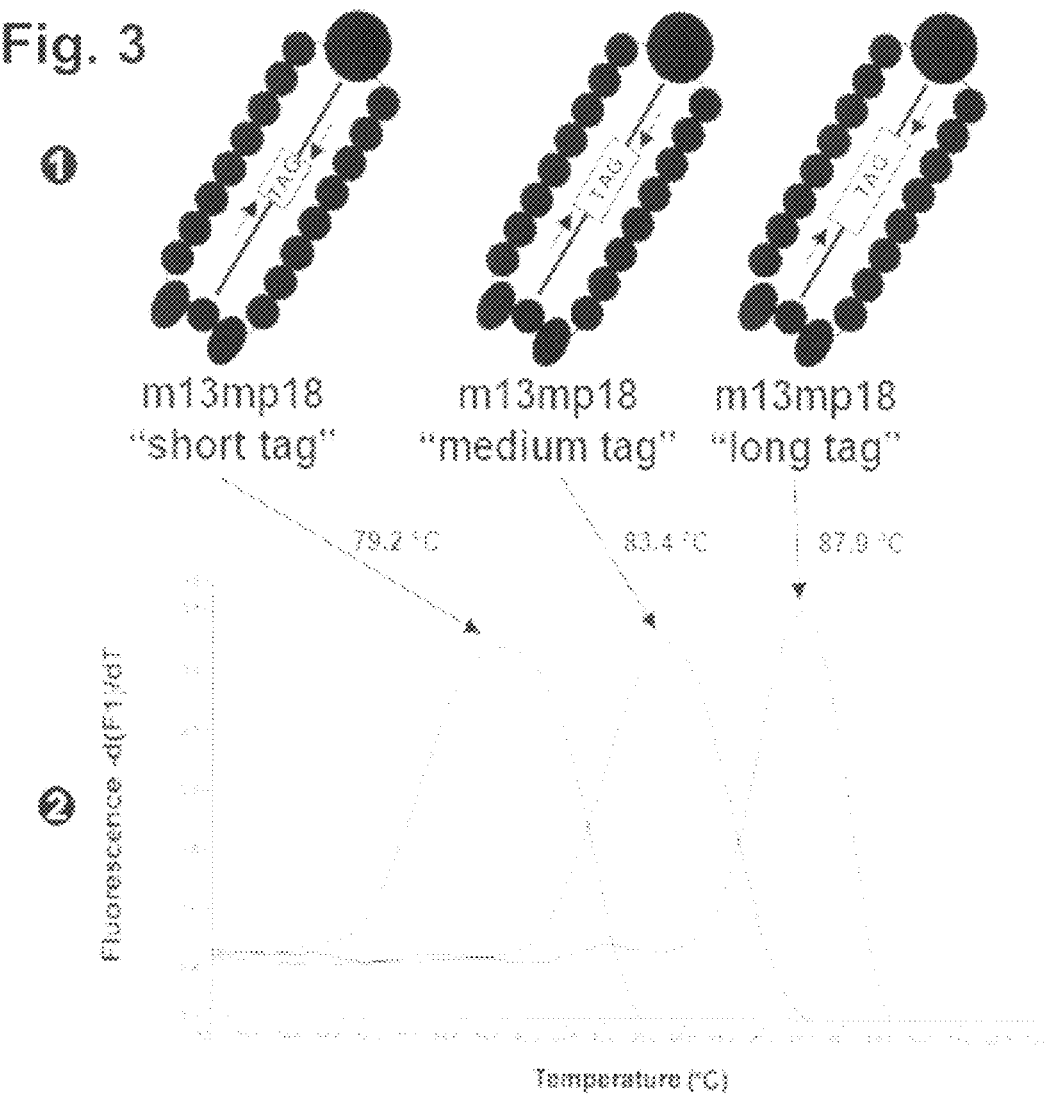
FIG. 3 is a series of images depicting differential melting curves for nucleic acid tags of differing lengths.

To test this approach, 3 types of m13 mp18 phage were created, in which type differed in the length of DNA tag between common PCR primer sites (FIG. 3). The phage were constructed by starting with m13mp18 phage DNA (New England Biolabs, Inc.) and digesting the multiple cloning site with either EcoRI/HincII restriction enzymes (to remove a ~35-bp stretch of DNA) or EcoRI/HindIII restriction enzymes (to remove a ~50-bp stretch of DNA). Digested DNAs were then individually Klenow-treated and blunt-end ligated back to one another. Following electroporation into E. coli cultures, the 3 types of phage were obtained, distinguished based on the identity of the tag contained within. By using a single pair of PCR primers that flanked the multiple cloning site (primers S1201S and S1211S, New England Biolabs), amplicons of 98 bp, 63 bp, and 47 bp were obtained from the uncut original, the EcoRI/HincII-digested, and EcoRI/HindIII-digested phages, respectively. When used as template DNA for fluorescent PCR and melting point analysis, unique tag melting points were confirmed (FIG. 3) (For additional detail regarding this "melting-curve" based method of nucleotide tag production and use, see also U.S. Patent Application Publication No. 2005-0136399 A1, U.S. patent application Ser. No. 10/971,933, which is hereby incorporated herein by reference in its entirety).

Figure 4:
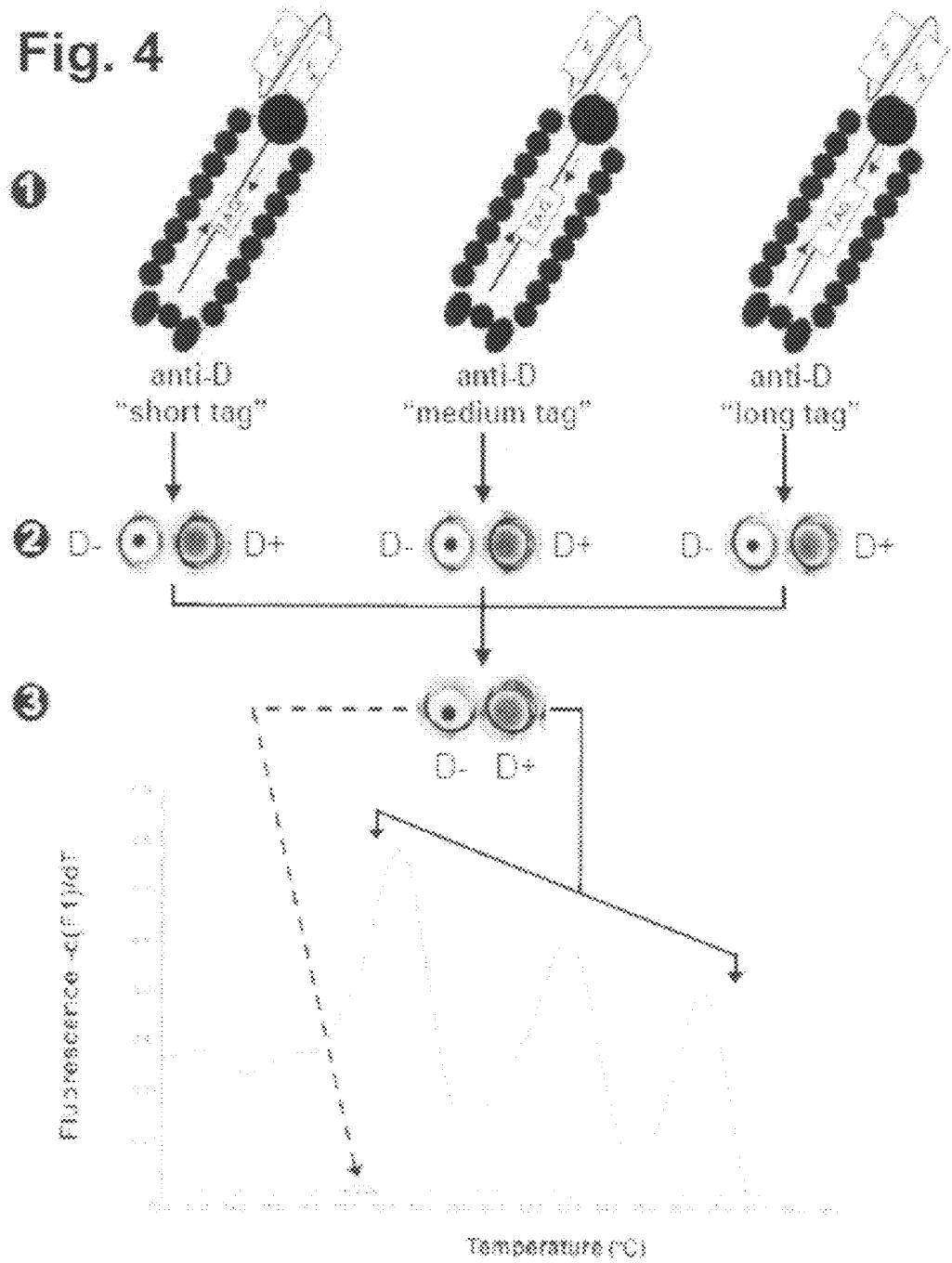
FIG. 4 is a series of images depicting differential melting curves for nucleic acid tags of differing lengths in a unlinked "phenotype/genotype" phage display experiment of the invention.

To demonstrate the ability to make antibody-displaying copy-protected phage, the heavy/light chain variable region DNA encoding the E1M2 anti-Rh(D) sequence was removed from the pComb3X phagemid vector, and re-cloned into an appropriately-prepared plasmid expression vector (PARA-H6-HIS). Following electroporation into E. coli, three separate aliquots of culture were infected with each type of m13 mp18 phage. This produced 3 types of phage particles, identical to the m13 mp18 versions, except that anti-Rh(D) was expressed on the surface (FIG. 4). After verifying that each version of anti-Rh(D) bound to Rh(D)-positive, but not Rh(D)-negative RBCs, aliquots of the 3 phage were combined, tested in a single pool for appropriate agglutination activity, and then subjected to fluorescent PCR and melting point analysis, as described in detail above. As shown in FIG. 4, simultaneous detection by reagent genotyping of all 3 versions of anti-Rh(D) to Rh(D)-positive RBCs was demonstrated. Negligible signal was detected in the Rh(D)-negative cell sampled (dotted line in FIG. 4). In fact, the melting point for the background signal coincided with the signal for a PCR water control (i.e. PCR with no phage DNA present) and was the result of primer-dimer formation, not non-specific binding anti-Rh(D) phage.

This set of experiments demonstrates a method for producing phage reagents that cannot be replicated by the end-user nor can the end-user determine the nucleotide sequence of the expressed antibody. Furthermore, the fact that the detection tag is introduced into the particle from the phage used for co-infection, obviates the need to clone tags into individual antibody constructs each time a different type of tag is desired in the final phage reagent product. The simultaneous binding and differentiation of each of the 3 types of anti-Rh(D) reagent to Rh(D)-positive cells but not Rh(D)-negative cells supports the concept of multiplexing phenotyping reactions, albeit in this example with 3 phage displaying the same specificity. The next sets of experiments will test the ability to multiplex phenotyping of cells for different specificities.

Experimental Example 3

Multiplexed Red Blood Cell Typing Reactions

To test the ability to multiplex typing reactions by phage reagent genotyping, an anti-blood group B phage reagent was created and mixed with one of the three anti-Rh(D) phage reagents set forth in Example 1. The admixture was incubated with RBCs of varying phenotype and binding was assessed by reagent genotyping.

Figure 5:
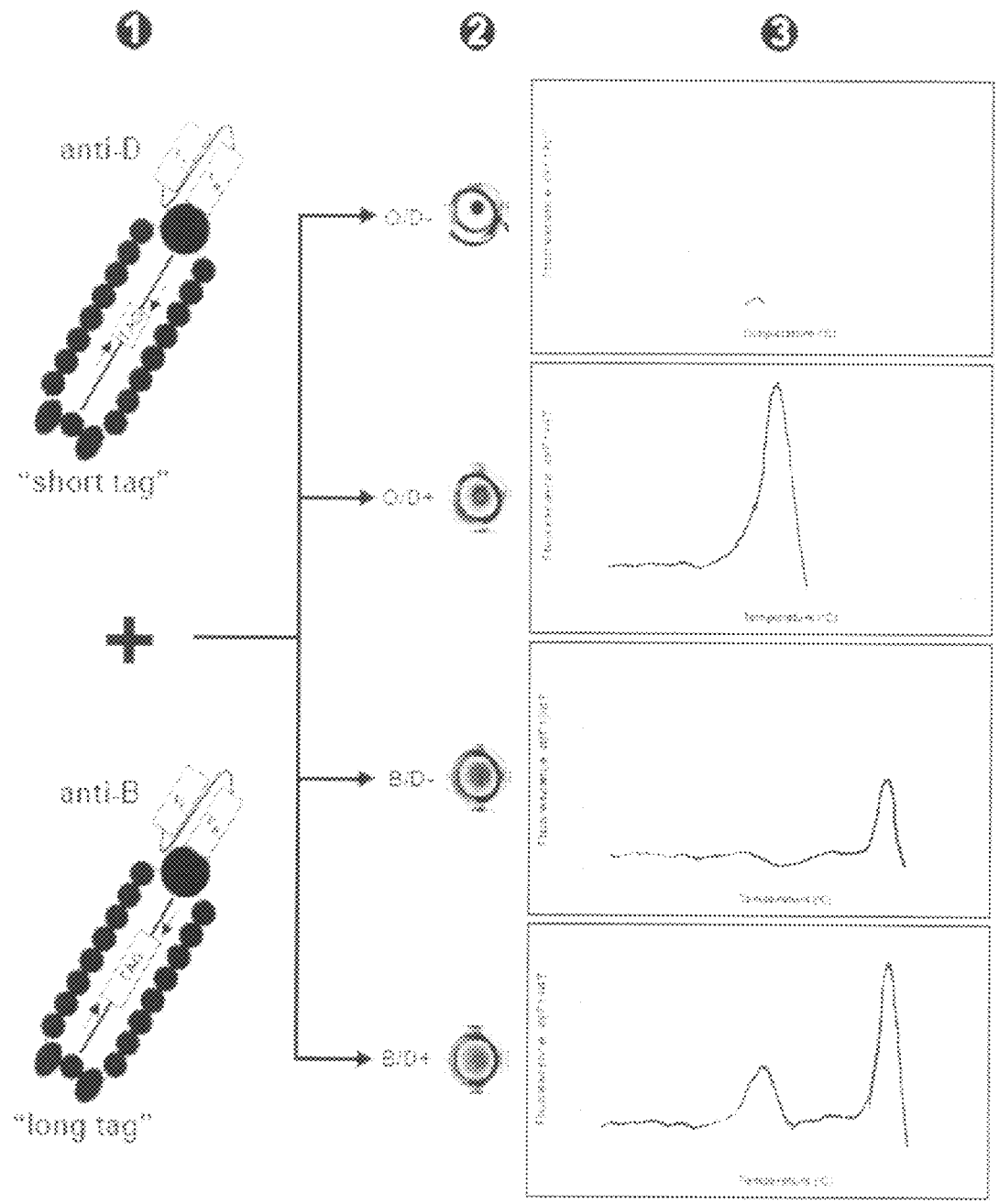
FIG. 5 is a series of images depicting differential melting curves used to identify multiple unique tags in a multiplexed phage reagent experiment of the invention.

An anti-B-expressing phage reagent was produced by subcloning a phage display-derived FB5.7 human anti-B clone out of a pComb3 phagemid vector into the pARA-H6-HIS plasmid vector as described above in Example 1. Following electroporation into E. coli, a "long-tag" m13 mp18 phage was used to produce anti-B phage. Anti-B phage was mixed with the "short-tag" version of anti-Rh(D) (FIG. 5) and incubated with either blood group O/Rh(D)-negative, O/Rh(D)-positive, B/Rh(D))-negative, or B/Rh(D)-positive RBCs. After washing, cell/phage preparations were resuspended in an anti-M13 antibody solution to verify appropriate cell agglutination patterns (FIG. 5). As described above for anti-Rh(D) phage reagent alone in Example 1, an aliquot of the cells, with or without bound phage, was diluted and used as template in a fluorescent PCR assay. Melting point analysis revealed the expected patterns of melting point peaks (FIG. 5).

Experimental Example 4

Additional Multiplex Red Blood Cell Typing Reactions

Because so few red blood cells are required per assay as set forth herein (150 cells vs. ~$10^7$ cells for conventional agglutination assays) and "lab-on-a-chip" types of platforms can offer multiple independent channels for cell/phage processing, thus facilitating extended antigen phenotyping, a second example was conducted to demonstrate the utility of phage reagent multiplexing. Rather than combining multiple specificities in one reaction, the possibility of combining phage to a single antigen with "negative control" phage (i.e. phage that should not bind to any red cell regardless of phenotype) and "positive control" phage (i.e. phage expressing an antibody that binds to essentially every RBC) was examined. With this scheme, each channel of a microfluidics chip provides information regarding the presence or absence of only one antigen, but in the presence of useful quality controls. To accomplish this, a phage was created expressing anti-desmoglein 3 (-dsg3), an antibody specific for a keratinocyte cell adhesion molecule which was previously isolated, using phage display, from a patient with pemphigus vulgaris. For a positive control, phage expressing anti-Rh17 was isolated, anti-Rh17 being an antibody that is specific to an epitope on the Rh(CE) protein which is present on RBCs from essentially 100% of the human population. This antibody had been previously isolated from a phage display library constructed from a macaque immunized with human RBCs.

Figure 6:
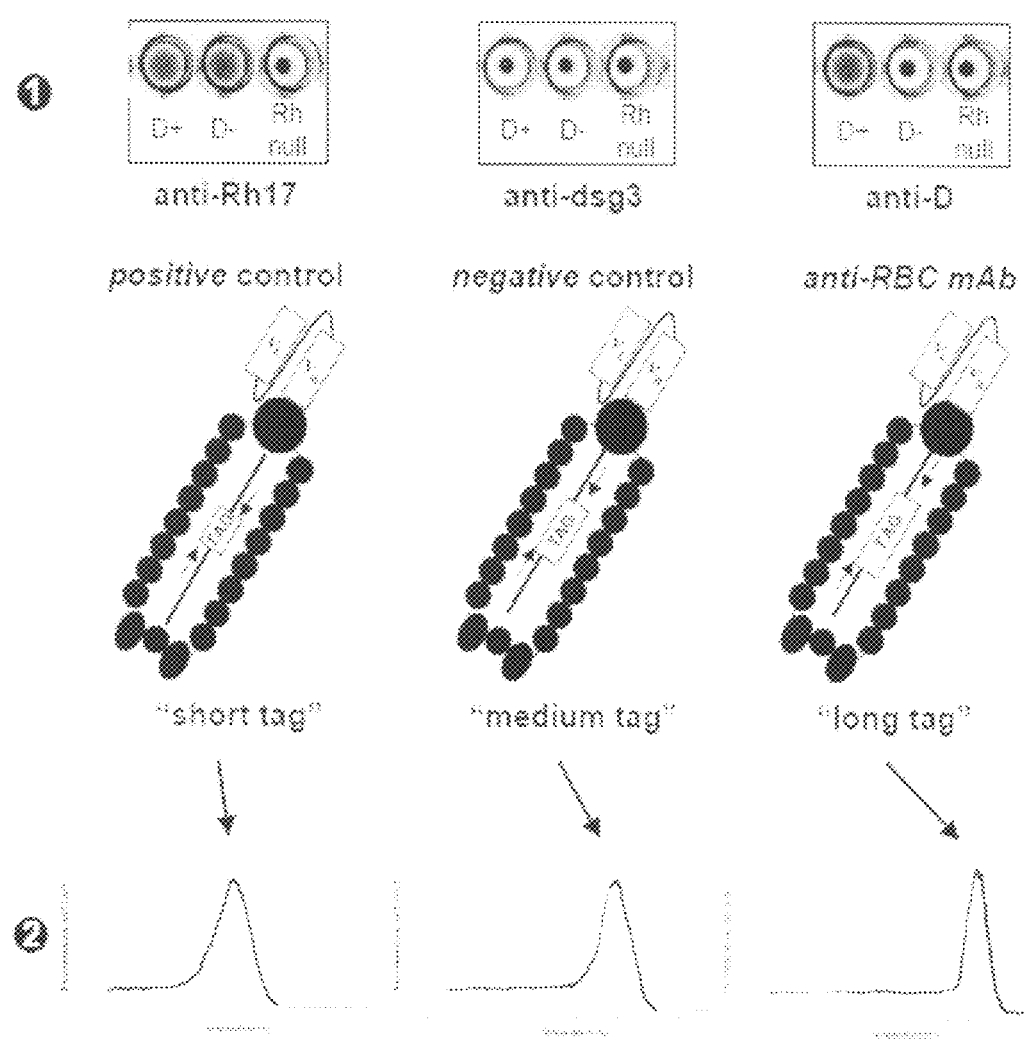
FIG. 6 is a series of images depicting differential melting curves used to identify the red cell binding characteristics and unique tags in a set of reagents used for multiplexed red blood cell typing experiments.

Anti-dsg3 and anti-Rh17 phage reagents were created by subcloning antibody clones PVE4-20 and MBK3-17 respectively, into the pARA-H6-HIS plasmid vector as described elsewhere herein for anti-Rh(D) and anti-B. "Medium tag" m13 mp18 was used to produce anti-dsg phage and "short-tag" m13 mp18 was used to produce anti-Rh17 phage. As shown in FIG. 6, each of these phages along with anti-Rh(D) clone E1M2 displayed the expected agglutination pattern when reacted with Rh(D)-negative, Rh(D)-positive, and $Rh_{null}$ RBCs ($Rh_{null}$ cells are extraordinarily rare and do not express the Rh17 or any other Rh antigens). FIG. 6 confirms the expected melting point temperatures for amplicons generated when the DNA tags from each of the 3 phage particles is amplified and analyzed.

Figure 7:
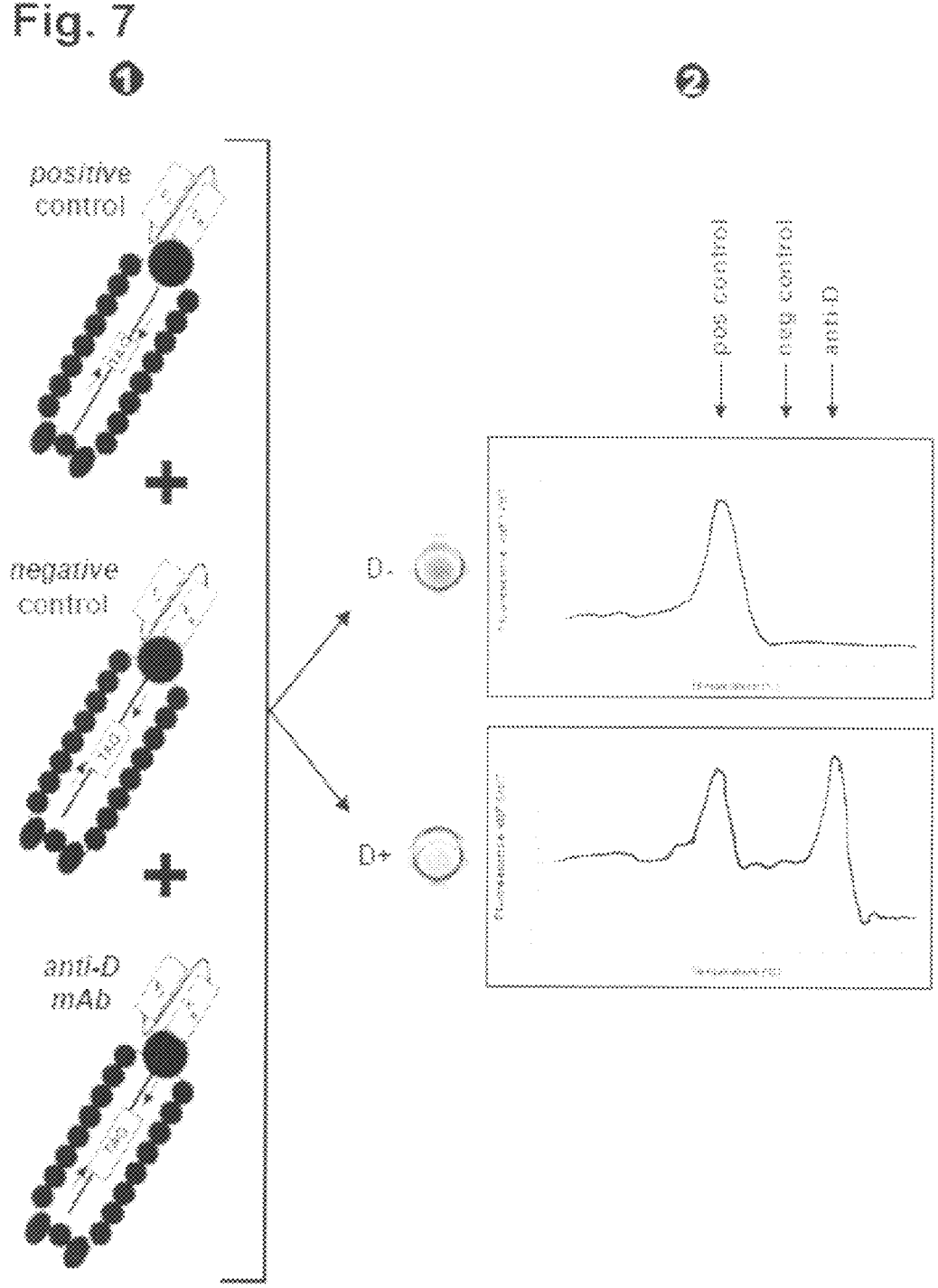
FIG. 7 is a series of images depicting differential melting curves used to identify multiple unique tags in a multiplexed red blood cell typing experiment.

Negative control phage (anti-dsg3), positive control phage (anti-Rh17), and anti-Rh(D) phage were then combined (FIG. 7) and incubated with Rh(D)-negative or Rh(D)-positive RBCs and processed for analysis. Melting point curves indicate binding of positive control phage to both cells, negative control phage to neither, and anti-Rh(D) phage to Rh(D)-positive RBCs only. This "quality control" aspect of the present invention was previously not possible with traditional methods of blood typing. Only with the present invention, and the multiplexing capabilities of the present invention, can both the positive and negative controls be included in a single assay.

Experimental Example 5

Phage Reagent Genotyping in Indirect Anti-globulin Tests

An essential component of pre-transfusion testing—and perhaps the most time consuming—is the screening of patient sera for the presence of pre-formed alloantibodies to blood group antigens. If any are found, red cells to be used for transfusion must be chosen that not only match for ABO/Rh(D), but lack antigen(s) to which the patient has previously developed immunity. Conventionally, alloantibody screening and identification are accomplished by incubating patient sera with reagent RBCs of known phenotype, washing, and resuspending RBCs in anti-human IgG ("indirect anti-globulin test"). If agglutination occurs with any of the reagent cells, the specificity(ies) of alloantibodies present (if any) in the patient's sera can be identified since the complement of antigens on each of the reagent red cells is known.

To determine the feasibility of performing indirect anti-globulin tests using our technology, human IgG-binding phage particles were created by expressing Staphylococcal protein A (SpA) on the surface of the particles. SpA is a cell wall component of Staphylococcal aureus well-known for its binding to the Fc domain (constant region) of IgG from a number of species, including human. Performance of antibody specificity identification panels were then performed by incubating a source of human IgG (either monoclonal IgG or serum-derived polyclonal IgG) with a set of 6 reagent panel cells (3 antigen-negative cells, 3 antigen-positive cells), washing, and then incubating with SpA phage. Following a second wash, the binding of SpA phage was assessed by detecting a DNA tag in the SpA particle.

M13 phage expressing the IgG-binding Domain B of SpA were produced as previously described (Djojonegoro et al., 1994, Bio/Technol. 12:169-172). A set of PCR primers was used to amplify a 95-bp stretch of DNA downstream to where the SpA-pIII was inserted into the PUC119 phagemid. As shown in FIG. 8, SpA phage DNA, when used as a template with these primers for PCR, yields amplicons with a melting point of ~81.5° C.

Figure 9A:
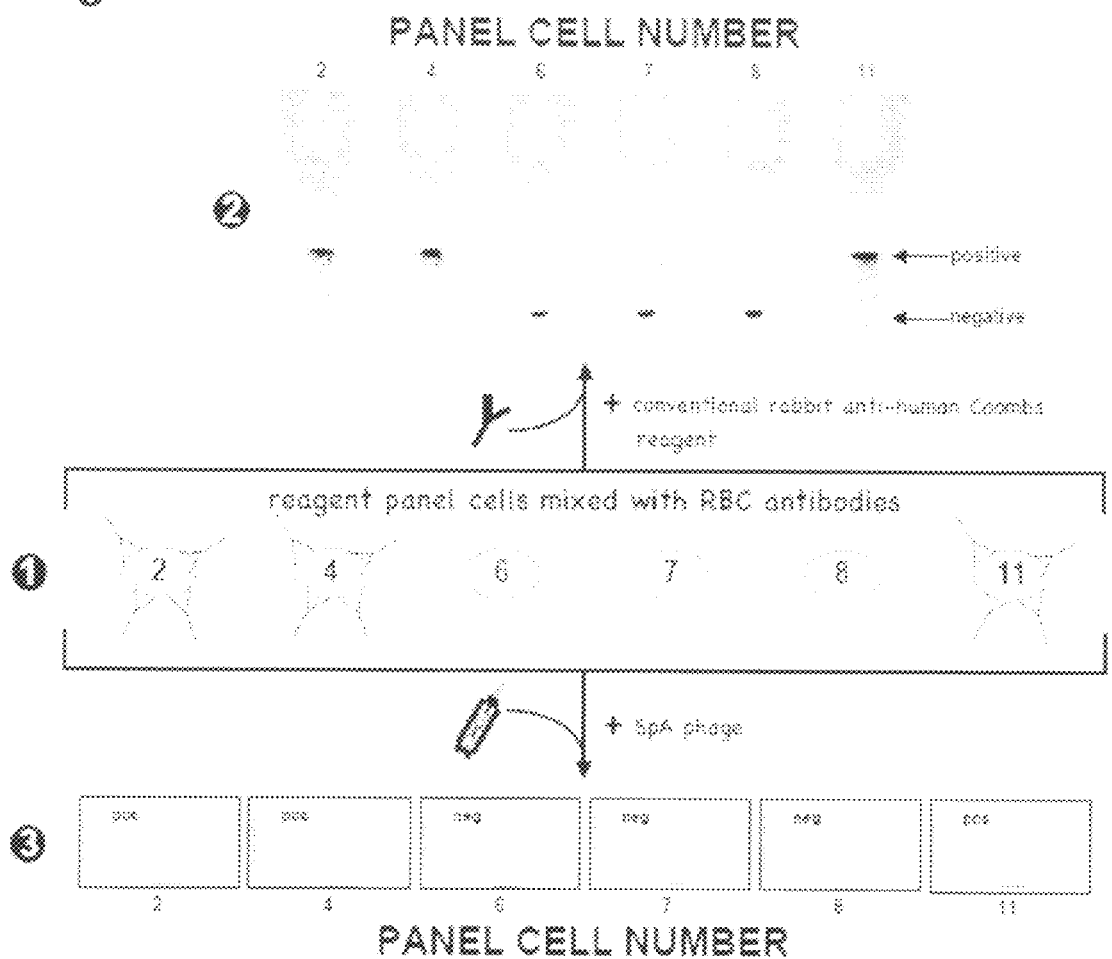
FIG. 9A is a series of images depicting the results of an indirect anti-globulin test performed according to the present invention illustrating the detection and specificity identification of a human monoclonal anti-Rh(D) antibody.

An antibody identification panel test was then performed by incubating reagent panel RBCs (Immucor) with human monoclonal anti-Rh(D) IgG in which cells #2, #4, and #11 were known to be Rh(D)-positive, and cells #6, #7, and #8 were known to be Rh(D)-negative (FIG. 9A, middle panel). The cells were then processed either in a conventional gel card assay (Ortho Clinical Diagnostics), in which rabbit anti-human globulin in the card induced agglutination in the appropriate samples (FIG. 9A, top panel), or were incubated with SpA phage, washed, and processed for SpA phage tag detection (FIG. 9A, bottom panel). Results with SpA phage were in perfect concordance with conventional agglutination procedures.

Figure 9B:
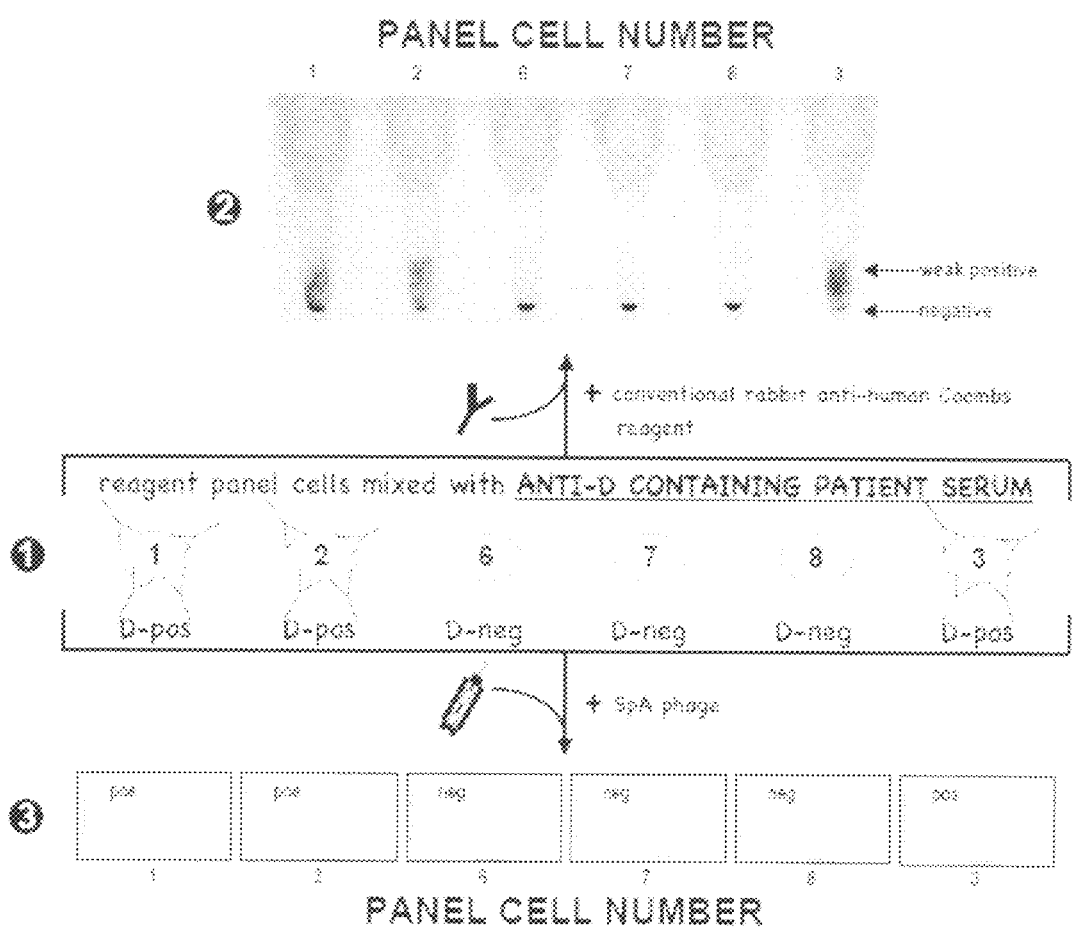
FIG. 9B is a series of images depicting the results of an indirect anti-globulin test performed according to the present invention illustrating the detection and specificity identification of human polyclonal anti-Rh(D) antibodies present in patient serum.
Figure 9C:
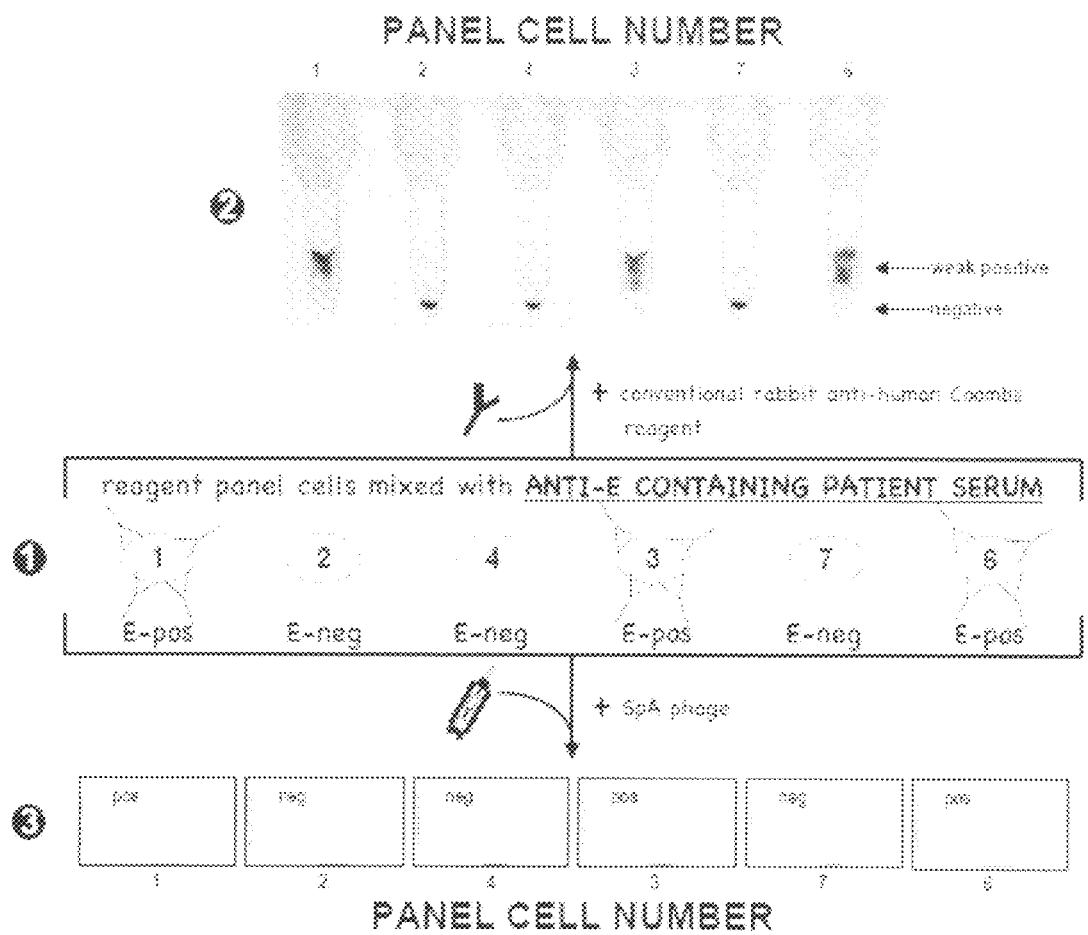
FIG. 9C is a series of images depicting the results of an indirect anti-globulin test performed according to the present invention illustrating the detection and specificity identification of human polyclonal anti-Rh(E) antibodies present in patient serum.

Analogous experiments were performed with authentic patient sera known to contain either anti-Rh(D) alloantibodies (FIG. 9B) or anti-Rh(E) alloantibodies (FIG. 9C). In the experiment depicted in FIG. 9B, the reagent red cells were known to be either Rh(D)-positive (cells #1, #2, and #3) or Rh(D)-negative (cells #6, #7, and #8). In the experiment depicted in FIG. 9C, the reagent red cells were known to be either Rh(E)-positive (cells #1, #3, # and #6) or Rh(E)-negative (cells #2, #4, and #7). As with the results shown in FIG. 9A, for the experiments depicted in FIGS. 9B and 9C, results with SpA phage (bottom panels) were in perfect concordance with conventional agglutination procedures (top panels).

These experiments demonstrate the feasibility of performing indirect anti-globulin tests using IgG-binding phage particles and reagent genotyping. As discussed in detail elsewhere herein, molecular genotyping utilizing a patient's genomic DNA cannot be used to conduct these time-consuming pre-transfusion tests since the serum-containing alloantibodies being tested for are not encoded in a patient's genome.

In another aspect of the invention, phage particle reagents can be prepared that express non-human (e.g. rabbit, mouse, chicken, etc.) mAbs (vs. SpA) which react with all 4 subclasses of human IgG. In addition, phage reagents can be created that express non-human monoclonal anti-human IgM or anti-human C3d which can be used to perform reverse ABO typings (i.e., detection of IgM anti-A and anti-B) and direct anti-globulin tests for RBC-bound complement fragment C3d.

Experimental Example 6

General Phage Display Technology

Also encompassed by the invention are RBC antigen-specific monoclonal antibodies which are displayed on the surface of filamentous bacteriophage particles (reviewed in Siegel, 2001, Transfusion Med. Rev. 15:35-52). In contrast to expensive and time-consuming conventional cellular methods for generating monoclonal antibodies from B-lymphocytes, antibody phage display works by immortalizing the immunoglobulin genes rather than the cells from which they were derived. By using molecular methods instead of cell transformation, "libraries" of phage particles are produced from populations of B-cells, each particle displaying a particular antibody specificity on the outside and containing the antibody's unique DNA sequence on the inside. The methods of the present invention provide for the production of bacteriophage that display a particular antibody specificity on the outside, and the bacteriophage do not contain the antibody's unique DNA sequence on the inside. That is, the bacteriophage produced according to the methods of the present invention do not have a phenotype (i.e., the antibody or antibody fragment displayed on the outer surface of the bacteriophage) that is linked to the bacteriophage genotype (i.e., the DNA contained within the bacteriophage), because there is no DNA contained within the bacteriophage that encodes the antibody displayed on the surface of the bacteriophage.

The methods of the present invention are similar to phage display methods well-known in the art, as described throughout the present specification. In addition, the methods of the present invention require the step of transforming an expression vector into a bacterial cell used to produce bacteriophage according to the present invention, wherein the expression vector comprises a nucleic acid sequence encoding the antibody or antibody fragment that will be displayed on the surface of the bacteriophage. By way of a non-limiting example, the nucleic acid encoding the antibody or antibody fragment is cloned in-frame with a bacteriophage coat protein, such that an antibody/coat protein fusion protein is expressed in the bacterial cell. This fusion protein is subsequently incorporated into the progeny bacteriophage that are produced according to the present invention.

Methods for selecting phage particles specific to particular cell-surface antigens from such libraries have been described previously (e.g., Siegel et al., 1997, J. Immunol. Meth. 206:73-85; U.S. Pat. No. 5,876,925, to Siegel) and hundreds of unique human anti-Rh(D) monoclonal phage-displayed antibodies have been produced to date (e.g., Siegel et al., 1997, J. Immunol. Meth. 206:73-85; Chang and Siegel, 1998, Blood 91:3066-3078; U.S. Pat. No. 6,255,455, to Siegel). Although monoclonal antibodies produced in this way can be expressed as soluble antibody molecules (unlinked to phage) that can agglutinate RBCs using the conventional indirect antiglobulin (i.e., Coombs) reaction (see Siegel and Silberstein, 1994, Blood 83:2334-2344), it has been established that the actual phage particles displaying the recombinant monoclonal antibodies can be used in agglutination reactions by substituting anti-M13 phage antibody for the Coombs reagent (Siegel et al., 1997, J. Immunol. Meth. 206:73-85; U.S. Pat. No. 5,985,543, to Siegel). An advantage of this method in agglutination assays using intact phage displaying the antibody is increased sensitivity since as few as approximately 10 anti-Rh(D)-expressing phage particles (compare with about 150-1000 conventional IgG) are needed to induce agglutination due to the greater degree of crosslinking by anti-M13 afforded by the relatively large size (approximately 0.5 microns) of the particles.

The substitution of conventional blood bank typing reagents with phage-displayed recombinant antibodies in agglutination assays is a vast improvement over prior art Coombs-based agglutination methodologies in and of itself for the reasons stated above—the ability to clone human antibodies without the need to B-cell transformation, greater assay sensitivity, inexpensive production in bacterial culture, and others (Siegel, 2001, Transfusion Med. Rev. 15:35-52).

Using antibody phage-display and other technologies available in the art, a set of novel monoclonal reagents specific for clinically-significant RBC antigens can be cloned, produced, and the performance characteristics thereof can be validate according to the teachings provided herein, as well as methods known in the art and to be developed in the future. For instance, previous studies demonstrated the production and isolation of such reagents with specificities for RBC antigens B, anti-Rh(D), M and N (see, e.g., Chang and Siegel, 2001, Transfusion. 41:6-12; Siegel et al., 1997, J. Immunol. Meth. 206:73-85; Chang and Siegel, 1998, Blood 91:3066-3078; Czerwinski et al., 1995, Transfusion. 35:137-144; Czerwinski et al., 1999, Transfusion. 39:364-371). Such methods can be applied to develop, among others, anti-A, anti-Rh(C, c, E, e), as well as antibodies in the Kell, Duffy, Kidd, and Ss blood groups. These reagents can be used in conventional manual and automated agglutination assays, as well as in the novel methods disclosed herein.

An index set of anti-blood group B and anti-Rh(D) phage can be produced and unique DNA sequence tags (i.e., beacon sequences), oligonucleotide primer and hybridization sites, and polymerase promoters inserted into the DNA that codes for each antibody. The performance characteristics of a number of nucleic acid amplification/detection schemes is assessed to identify and quantify the RBC binding of each reagent as exemplified herein using group B and anti-Rh(D) phage reagents. Polymerase chain reaction (PCR) and agarose gel electrophoresis can be used to simultaneously detect and differentiate the binding of two different anti-RBC antibody specificities.

Amplification of Phage DNA Using the Polymerase Chain Reaction:

In one aspect, the binding of a RBC-specific phage-displayed antibody, e.g., a phage particle expressing anti-Rh(D), can be detected through the addition of oligonucleotide primers specific to the anti-Rh(D)'s nucleic acid sequence exposed when, for example, the bound phage particles are heated to denature the phage coat. One primer can be complementary to a generic sequence contained in the phage DNA (irrespective of antibody specificity) and the other primer can be complementary to, e.g., a sequence specific to that phage, such as, but not limited to, the CDR3 hypervariable region of the antibody's heavy chain (i.e., the sequence that is unique for a given antibody). The measurement of the resultant amplified antibody DNA can indicate the presence of that antibody's cognate antigen on the surface of a cell being examined. Without wishing to be bound by any particular theory, a number of different phage-displayed blood group antibodies can be contacted simultaneously to the same sample of red cells and the differences in antibody nucleotide sequence can be exploited to determine which ones bound and which ones did not as demonstrated herein using anti B and anti-Rh(D) antibodies displayed on different phage. Such "multiplexing" is not possible by agglutination methods as one could never tell which antibody(ies) caused the agglutination.

The skilled artisan, based upon the disclosure provided herein, would readily appreciate that such "multiplexing" strategy is not limited to any particular antibodies, but can be used to detect multiple red blood cell antigens using a wide plethora of antibody-displaying phage, where each phage comprises a DNA sequence that can be detectably distinguished from the nucleic acid of other phage encoding antibodies having different specificities, or even phage encoding antibodies having the same specificities, so long as the nucleic acids of the phage can be distinguished from one another. Using PCR and agarose gel electrophoresis to amplify and then detect unique coding sequences within each type of phage particle based on, e.g., size of the amplicons, a sample of RBCs can be simultaneously phenotyped for B and Rh(D) with extraordinary sensitivity when compared to a conventional agglutination reaction.

In practice, however, a rapid, scaleable, and automatable DNA readout can be used instead of agarose gel electrophoresis. Many methods are well-known in the art, and several such methods are discussed more fully elsewhere herein. Nonetheless, the skilled artisan would understand, once armed with the teachings of the invention, that a wide plethora of methods to detect nucleic acids can be used in the methods of the invention, and the invention is not in any way limited to the methods exemplified and discussed herein.

Amplification of Phase DNA Using Transcription-Mediated Amplification

In addition to using PCR for phage DNA amplification step, methods based on detection of transcription of phage antibody DNA, instead of its amplification, can be used in the methods of the invention. More specifically, immunodetection by this method can be used to detect the binding of antibodies to which oligonucleotides containing the T7 RNA polymerase promoter site have been chemically-conjugated with glutaraldehyde as described in Zhang et al. (2001, Proc. Natl. Acad. Sci. USA 98:5497-5502), This technique for the transcription of DNA that is attached in vivo to an antibody by virtue of its physical association in phage particles can be used as an alternative to PCR and other amplification techniques. This technology has been termed IDAT, which stands for immuno-detection amplified by T7 RNA (Zhang et al., 2001, Proc. Natl. Acad. Sci. USA 98:5497-5502). By placing the T7 RNA polymerase promoter site upstream from an arbitrary sequence tag in the phagemid DNA, the addition of T7 RNA polymerase and NTPs rapidly (100 bases per second) produces tag transcripts through the consecutive and progressive binding of T7 enzymes to their promoter.

Since T7 RNA polymerase binding to RNA products does not occur, amplification is linear not exponential as in PCR. For RBC phenotyping, such linear amplification provides an advantage over PCR (and certainly over conventional agglutination methods) in that quantitative information (i.e., relative antigen copy number per cell) about multiple antigens can be determined simultaneously from a single sample of cells. An example, among others, of where such quantification can be useful in blood banking is the detection of "weak Rh(D)" phenotypes as reviewed in Mollison et al. (1997, In: Blood Transfusion in Clinical Medicine, 10th ed., Blackwell Scientific Publications, Oxford, England).

An additional advantage of transcription-based detection methods, such as, but not limited to, IDAT, over PCR is elimination of temperature cycling once the antibody phage DNA is released from the particles. Elimination of temperature cycling reactions simplify instrument design and lowers cost of the assay. Nevertheless, PCR and transcription methods each have advantages and disadvantages that are well-known in the art such that the skilled artisan can readily determine which method, or any other method, can be used for any particular assay and the conditions desired therefor. This is because PCR, transcription, and many other methods to detect a nucleic acid, can be used successfully in the methods of the present invention and the skilled artisan would appreciate what method to employ based on art-recognized factors.

Detection of Phage DNA Using Molecular Beacons:

Molecular beacons are stem-and-loop-structured oligonucleotides with a fluorescent label at the 5' end and a universal quencher at the 3' end (see, e.g., Tyagi and Kramer, 1996, Nature Biotech. 14:303-308; Broude, 2002, Trends in Biotechnology 20:249-256). When the stem is closed (in the absence of complementary nucleic acid), the fluorophore and quencher are in close proximity and fluorescent energy is absorbed by the quencher and fluorescence is quenched and not detectable. In the presence of complementary nucleic acid, the loop of the beacon hybridizes and the fluorophore and quencher separate such that quenching does not occur. Photons are then emitted from the fluorophore, unquenched, at the wavelength specific for that fluorophore and fluorescence is then detectable. By combining a number of beacons in one tube, each with a different fluorophore at their 5' ends, multiple DNA (Tyagi et al, 1998, Nature Biotech. 16:49-53) or RNA (de Baar et al., 2001, J. Clin. Microbiol. 39:1895-1902) targets can be simultaneously detected by measuring the spectrum of colors emitted from the reaction vessel.

Molecular beacons of two different colors are incorporated into the PCR and transcription reactions to detect the presence of antibody-specific DNA. As described elsewhere herein, anti-Rh(D) and anti-B phage DNA are modified to contain short DNA sequences that can be amplified (or transcribed) and subsequently detected using molecular beacons as described elsewhere herein. The design an production of such "beacon" sequences, and nucleic acid sequences comprising sequences "complementary" thereto are well known in the art. Indeed, software programs are commercially available to assist in the design of such sequences, including the molecular beacon probe sequences complementary to a sequence of interest.

Further, such beacons and sequences that bind therewith, such as those exemplified in FIG. 4, comprise the following sequences: the sequence of the "B140" insert is

```
                                    (SEQ ID NO: 1)
5'-TGCTATGTCACTTCCCCTTGGTTCTCTCATCTGGCCTGGTGCAAT

AGGCCCTGCATGCACTGGATGCACTCTATCCCATTCTGCAGCTTCCTC

ATTGATGGTCTCTTTTAACATTTGCATGGCTGCTTGATGTCCCCC

CACT-3'
``` and the sequence of the "D140" insert is

```
                                    (SEQ ID NO: 2)
5'-TGCTATGTCACTTCCCCTTGGTTCTCTCATCTGGCCTGGTGCAAT

AGGCCCTGCATGCACTGGATGCACTCTGTTTTACCTCATTATCCTTCT

GCCAGCGCTAGCTTTTAACATTTGCATGGCTGCTTGATGTCCCCCCAC

T-3'.
```

The forward PCR primer ("PCR-F") is:

```
                                    (SEQ ID NO: 3)
    5'-TGCTATGTCACTTCCCCTTGGTTCTCT-3'
``` and the reverse PCR primer ("PCR-R") sequence is:

```
                                    (SEQ ID NO: 4)
    5'-AGTGGGGGACATCAAGCAGCCATGCAAAT-3'.
```

The B-Beacon and D-Beacon sequences are as follows, showing the fluorescent derivatives at the ends and the stem structures in lower case letters. The "B-Beacon" sequence is as follows:

```
                                    (SEQ ID NO: 5)
6-FAM-gcgagcATCCCATTCTGCAGCTTCCTCATTGATGGTCTCgctc
gc-DABCYL.
```

The "D-Beacon" is:

```
                                    (SEQ ID NO: 6)
TAMRA-cgagcGTTTTACCTCATTATCCTTCTGCCAGCGCTAGCgctc
gc-DABCYL.
```

The upper case letters in the beacon sequences represent the respective sequences in B140 and D140 to which the beacons anneal. Therefore, the upper case letters are the sequences of the oligonucleotides that are used for the DNA array detection. That is, a "B-oligo" is:

```
                                    (SEQ ID NO: 7)
    5'-ATCCCATTCTGCAGCTTCCTCATTGATGGTCTC-3',
``` and a "D-oligo" is:

```
                                    (SEQ ID NO: 8)
    5'-GTTTTACCTCATTATCCTTCTGCCAGCGCTAGC-3'.
```

The present invention is not limited to these exemplary sequences; rather, the invention encompasses such additional sequences as can be readily designed by the skilled artisan once armed with the disclosure provided herein. That is, the design and use of beacon sequences are well-known in the art and are not discussed further herein and the sequences disclosed herein are merely an example of the sequences that can be used to practice the invention. For instance, many fluorescer-quencher pairs are known in the art, including, but not limited to, those exemplified herein which encompass 6-carboxyfluorescein (6-FAM), 6-carboxytetramethylrhodamine (TAMRA), and DABCYL (a non-fluorescent chromophore that serves as a universal quencher for any fluorophore in a molecular beacon: 4-(4-dimethylaminophenylazo)-benzoic acid). Such molecules are well known in the art, and are described in, e.g., U.S. Pat. Nos. 6,395,517, and 6,615,063, and are not discussed further herein.

Detection of Phage DNA Using Oligonucleotide Microarrays:

In addition to molecular beacons, hybridization of fluorescent RBC phage antibody amplicons (from PCR) or transcripts (produced using IDAT) to arrays of complementary oligonucleotide probes can be used to indirectly quantify the amount (if any) of bound antibody in a sample. Further, although the use of conventional methods for hybridization to such microarrays are diffusion limited and may require several hours to obtain adequate fluorescent signals, this process can be accelerated by 2-3 orders of magnitude through the application of an electric field across the surface of an inexpensive indium tin oxide-coated glass slide as described in Su et al. (2002, Electrophoresis 23:1551-1557). This process, known in the art as "electric field-accelerated hybridization to oligonucleotide microarrays" provides rapid results, e.g., time from application of DNA (or RNA) to readout is less than about 10 minutes. Therefore, electric field-accelerated hybridization can be used to further enhance the rapid detection of antigens of interest present on a cell (e.g., a red blood cell, a platelet, and the like).

The present invention is not limited to blood typing, but has wide potential uses in many other areas of transfusion medicine, such as, but not limited to, platelet antigen testing, and has broad application in transplantation immunology (HLA antigen typing) and particularly forensic medicine, where multiplexing of reactions can provide the most amount of information from minute amounts of testing samples. In addition, the construction of antiglobulin reagents (e.g., anti-IgG, -IgM, -C3 complement component) expressed on phage particles can be used to perform serum screening for pre-formed anti-RBC antibodies, reverse group typing, or to perform direct/indirect Coombs tests using a methodology that detects the antiglobulin reagents' associated DNA. The antiglobulin phage reagents can be isolated from immune murine phage display libraries, or through the cloning of pre-existing hybridoma immunoglobulin mRNA using techniques well-known in the art.

The disclosures of each and every patent, patent application, and publication cited herein are hereby incorporated herein by reference in their entirety.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed:

1. A method of generating an antibody-displaying bacteriophage that does not contain a nucleic acid sequence encoding the displayed antibody, the method comprising the steps of:
   a) administering a non-phage vector comprising a nucleic acid that lacks a phage packaging sequence to a bacterial cell, wherein the nucleic acid encodes a fusion protein comprising an antibody and a polypeptide that will be displayed on the outer surface of a bacteriophage, and wherein the bacterial cell produces the fusion protein;
   b) infecting the bacterial cell with a phage, wherein the phage comprises a detectable marker molecule, wherein phage particles are produced in the bacterial cell; and
   c) assembling a bacteriophage in the bacterial cell, wherein the bacteriophage comprises the detectable marker molecule and displays the fusion protein on its outer surface and does not contain the nucleic acid sequence encoding the displayed antibody.

2. The method of claim 1, wherein the marker molecule is selected from the group consisting of a marker nucleic acid, a fluorescent molecule, a polypeptide, a lipid, a carbohydrate, a ligand, a receptor, an enzyme, a substrate, and an inorganic molecule.

3. The method of claim 1, wherein the antibody binds specifically to a red blood cell antigen.

4. The method of claim 3, wherein the red blood cell antigen is selected from the group consisting of A, B, Rh(D), Rh(C), Rh(c), Rh(E), Rh(e), K, k, $Js^a$, $Js^b$, $Kp^a$, $Le^a$, $Le^b$, $Lu^a$, $Lu^b$, $Fy^a$, $Fy^b$, M, N, S, s, $Do^a$, $Do^b$, $Jk^a$, and $Jk^b$.

5. The method of claim 1, wherein the antibody binds specifically to an antigen selected from the group consisting of a lymphocyte antigen, a monocyte antigen, and a granulocyte antigen.

6. The method of claim 1, wherein antibody binds specifically to a platelet antigen.

7. The method of claim 6, wherein the platelet antigen is selected from the group consisting of HPA-1a, HPA-1b, HPA-2a, HPA-2b, HPA-3a, HPA-3b, HPA-4a, HPA-4b, HPA-5a, HPA-5b, HPA-6b, HPA-7b, HPA-8b, HPA-9b, HPA-10b, $Gov^a$, and $Gov^b$.

8. The method of claim 1, wherein the marker molecule comprises a nucleic acid sequence complementary to a molecular beacon probe.

9. The method of claim 8, wherein the molecular beacon probe comprises a fluorophore.

10. The method of claim 2, wherein the marker molecule is a marker nucleic acid.

11. A kit for detecting the presence of an antigen-bearing moiety on a cell, the kit comprising the bacteriophage generated according to the method of claim 1;
the kit further comprising an applicator and an instructional material for the use thereof.

12. A method of detecting the presence of an antigen-bearing moiety on a cell, the method comprising the steps of:
a) generating an antibody-displaying bacteriophage according to the method of claim 1;
b) contacting a cell with the bacteriophage;
c) denaturing any bacteriophage specifically bound with the cell to release the marker molecules; and
d) detecting the marker molecules, wherein detecting the marker molecule detects the presence of the antigen-bearing moiety on the cell.

13. A method of detecting the presence of at least two different antigen-bearing moieties on a cell, the method comprising the steps of:
a) generating a first antibody-displaying bacteriophage with a first marker molecule according to the method of claim 1;
b) generating a second antibody-displaying bacteriophage with a second marker molecule according to the method of claim 1;
c) contacting the cell with the first bacteriophage;
d) contacting the cell with the second bacteriophage;
e) detecting the binding of the first bacteriophage with the first antigen-bearing moiety by detecting the presence of the first marker molecule, wherein detecting the first marker molecule detects the presence of the first antigen-bearing moiety on the cell; and
f) detecting the binding of the second bacteriophage with the second antigen-bearing moiety by detecting the presence of the second marker molecule, wherein detecting the second marker molecule detects the presence of the second antigen-bearing moiety on the cell.

14. The method of claim 13, wherein the first marker molecule is a first marker nucleic acid, and further wherein the second marker molecule is a second marker nucleic acid.

15. The method of claim 14, wherein the first and second marker nucleic acids are detected by assaying the melting temperatures of the first and the second marker nucleic acids.

16. A method of detecting the presence of an anti-red blood cell antibody in human serum, the method comprising the steps of:
a) contacting a human red blood cell expressing at least one human red blood cell antigen on the surface of the cell with the serum;
b) washing the cell to remove any antibody bound non-specifically with the cell;
c) generating an anti-human globulin reagent-displaying bacteriophage according to the method of claim 1, wherein the antibody is the anti-human globulin reagent;
d) contacting the cell with the bacteriophage;
e) washing the cell to remove any bacteriophage bound non-specifically with the cell;
f) denaturing the bacteriophage specifically bound with the cell to release the marker molecule; and
g) detecting the marker molecule, wherein detecting the marker molecule detects the presence of the anti-red blood cell antibody in the serum.

17. A method of detecting the presence of an anti-red blood cell antibody in a human, the method comprising the steps of:
a) obtaining a red blood cell from the human;
b) washing the cell to remove any antibody bound non-specifically with the cell;
c) generating an anti-human globulin reagent-displaying bacteriophage according to the method of claim 1, wherein the antibody is the anti-human globulin reagent;
d) contacting the cell with the bacteriophage;
e) denaturing the bacteriophage specifically bound with the cell to release the marker molecule; and
f) detecting the marker molecule, wherein detecting the marker molecule detects the presence of the anti-red blood cell antibody in the human.

18. A method of detecting the presence of an antigen-bearing moiety in a composition, the method comprising the steps of:
a) generating an antibody-displaying bacteriophage according to the method of claim 1;
b) contacting the composition with the bacteriophage; and
c) detecting the marker molecule, wherein detecting the marker molecule detects the presence of the antigen-bearing moiety on the cell.

19. The method of claim 12, further comprising amplifying the marker molecule prior to step (d).

20. The method of claim 12, the method further comprising washing the cell between step (b) and step (c).

21. The method of claim 19, wherein the marker molecule is amplified using polymerase chain reaction (PCR).

22. The method of claim 19, wherein the marker molecule is amplified by transcription using immuno-detection amplified by T7 RNA (DAT).

23. The method of claim 19, wherein the marker nucleic acid is detected by assaying the melting temperature of the marker nucleic acid.

* * * * *

UNITED STATES PATENT AND TRADEMARK OFFICE
CERTIFICATE OF CORRECTION

| | | |
|---|---|---|
| PATENT NO. | : 9,658,224 B2 | Page 1 of 1 |
| APPLICATION NO. | : 12/085618 | |
| DATED | : May 23, 2017 | |
| INVENTOR(S) | : Donald Siegel et al. | |

It is certified that error appears in the above-identified patent and that said Letters Patent is hereby corrected as shown below:

In the Specification

In Column 1, after the title, STATEMENT REGARDING FEDERALLY SPONSORED RESEARCH OR DEVELOPMENT, please replace the paragraph at Lines 18-21 with the following paragraph:

--This invention was made with government support under grant number HL073533, HL002621, and HL054516 awarded by the National Institutes of Health. The government has certain rights in the invention.--

Signed and Sealed this
Twelfth Day of February, 2019

Andrei Iancu
*Director of the United States Patent and Trademark Office*